US008741599B2

(12) United States Patent
Pompejus et al.

(10) Patent No.: US 8,741,599 B2
(45) Date of Patent: *Jun. 3, 2014

(54) FERMENTATIVE PRODUCTION OF ORGANIC COMPOUNDS

(75) Inventors: Markus Pompejus, Seoul (KR);
Stephan Freyer, Neustadt (DE);
Markus Lohscheidt, Heidelberg (DE);
Oskar Zelder, Speyer (DE); Matthias Boy, Langen (DE)

(73) Assignee: BASF SE (DE)

( * ) Notice: Subject to any disclaimer, the term of this patent is extended or adjusted under 35 U.S.C. 154(b) by 1052 days.

This patent is subject to a terminal disclaimer.

(21) Appl. No.: 12/094,626

(22) PCT Filed: Nov. 27, 2006

(86) PCT No.: PCT/EP2006/068926
§ 371 (c)(1),
(2), (4) Date: May 22, 2008

(87) PCT Pub. No.: WO2007/060233
PCT Pub. Date: May 31, 2007

(65) Prior Publication Data
US 2008/0299606 A1 Dec. 4, 2008

(30) Foreign Application Priority Data
Nov. 28, 2005 (DE) .......................... 10 2005 056 668

(51) Int. Cl.
C12P 23/00 (2006.01)
C12P 19/14 (2006.01)
C12P 19/02 (2006.01)
C12P 13/04 (2006.01)
C12P 13/08 (2006.01)
C12P 13/00 (2006.01)
C12P 7/66 (2006.01)
C12P 1/00 (2006.01)
C12P 19/38 (2006.01)
C12P 7/14 (2006.01)
C12N 1/00 (2006.01)
C12N 1/20 (2006.01)

(52) U.S. Cl.
USPC ............... 435/67; 435/99; 435/105; 435/106; 435/115; 435/128; 435/134; 435/136; 435/139; 435/144; 435/158; 435/41; 435/69.1; 435/87; 435/88; 435/89; 435/162; 435/243; 435/252.3

(58) Field of Classification Search
USPC ............ 435/67, 99, 105, 106, 115, 128, 134, 435/136, 139, 144, 158, 41, 69.1, 87, 88, 435/89, 162, 243, 252.3
See application file for complete search history.

(56) References Cited

U.S. PATENT DOCUMENTS

| 3,787,587 | A | 1/1974 | Weber |
| 4,306,023 | A | 12/1981 | Crombie |
| 4,963,486 | A * | 10/1990 | Hang ............................ 435/139 |
| 7,820,419 | B2 * | 10/2010 | Smith et al. ................... 435/161 |
| 2002/0079268 | A1 | 6/2002 | Caboche et al. |
| 2004/0017023 | A1 | 1/2004 | Schoemann et al. |
| 2004/0048344 | A1 | 3/2004 | Baldenius et al. |
| 2004/0063184 | A1 * | 4/2004 | Grichko ........................ 435/161 |
| 2008/0254515 | A1 * | 10/2008 | Boy et al. ..................... 435/71.1 |
| 2008/0318287 | A1 * | 12/2008 | Boy et al. ..................... 435/115 |
| 2009/0162892 | A1 * | 6/2009 | Pompejus et al. .............. 435/67 |
| 2009/0226571 | A1 * | 9/2009 | Freyer et al. .................... 426/61 |

FOREIGN PATENT DOCUMENTS

| CA | 2 549 171 | 6/2005 |
| CA | 2 566 475 | 12/2005 |
| CN | 1173541 | 2/1998 |
| CN | 1218111 | 6/1999 |
| CN | 1266102 | 9/2000 |
| CN | 1321772 A | 11/2001 |
| DE | 3146558 A1 | 6/1983 |
| DE | 3731293 | 4/1989 |
| DE | 19519270 A1 | 12/1996 |
| EP | 0287152 A1 | 10/1988 |
| EP | 1205557 | 5/2002 |
| JP | 56-169594 | 12/1981 |

(Continued)

OTHER PUBLICATIONS

Pfefferle, et al., "Biotechnological Manufacture of Lysine," *Advances in Biochemical Engineering*, vol. 79, pp. 59-112, 2003.
Beukema, et al. "Production of Fermentation Syrups by Enzymatic Hydrolysis of Potatoes," *Biotechnological Research in the Netherlands*, 6, 1983.

(Continued)

*Primary Examiner* — Ganapathirama Raghu
(74) *Attorney, Agent, or Firm* — Novak Druce Connolly Bove + Quigg LLP

(57) ABSTRACT

A process for the fermentative production of at least one organic compound having at least 3 C atoms or having at least 2 C atoms and at least one 1 N atom, comprising the following steps:
a1) milling a starch feedstock, thus obtaining a millbase which comprises at least part of the nonstarchy solid constituents of the starch feedstock;
a2) suspending the millbase in an aqueous liquid and hydrolysis of the starch portion in the millbase by enzymatic liquefaction and, if appropriate, subsequent saccharification, whereby a first liquid (1) which comprises mono- or oligosaccharides is obtained; and
b) addition of the liquid (1) which comprises mono- or oligosaccharides together with metabolizable mono-, di- or oligosaccharides or together with a composition which comprises metabolizable mono-, di- or oligosaccharide in a concentration of at least 50% by weight and which is essentially free from solids which are insoluble in water to a fermentation medium comprising a microorganism which is capable of overproducing the organic compound under fermentation conditions.

18 Claims, No Drawings

(56) References Cited

FOREIGN PATENT DOCUMENTS

| | | | |
|---|---|---|---|
| JP | 57-159500 | 10/1982 | |
| JP | 2001-072701 | 3/2001 | |
| JP | 2001/275693 | 10/2001 | |
| JP | 2001/309751 | 11/2001 | |
| JP | 2001-309751 * | 11/2001 | ............... A23K 1/16 |
| JP | 2003-164265 A | 6/2003 | |
| JP | 2003-259892 A | 9/2003 | |
| NL | 8302229 | 1/1985 | |
| WO | WO-98/55599 | 12/1998 | |
| WO | WO-02/066663 | 8/2002 | |
| WO | WO-02/077252 | 10/2002 | |
| WO | WO-2004/113551 | 12/2004 | |
| WO | WO-2005/059144 | 6/2005 | |
| WO | WO-2005/116228 | 12/2005 | |
| WO | WO-2007/028804 | 3/2007 | |

OTHER PUBLICATIONS

Mersmann, et al. "Selection and Design of Aerobic Bioreactors," Ehem. Eng. Technol., 13, 1990, pp. 357-370.

"Getreide," [Grain] RÖMPP Online, version 3.9, (German language) last accessed Nov. 24, 2010.

"Begleitalkohol," [by-product formation during alcoholic fermentation] Wikipedia.de entry, (German language) last accessed Dec. 13, 2010.

"Bioethanol-Produktionsverfahren" [Bioethanol production methods] Crop Energies AG, (German language), http://www.cropenergies.com/de/Biotethanol/Produktionsverfahren, page last updated Aug. 6, 2009.

Atwell, "Wheat Flour", *Eagan Press Handbook Series*, Ch. 2, (2001), pp. 18-22.

Botterbrodt et al., "Handbuch Mehl-und Schälmüllerei", vol. 3, (2008) pp. 49-50, pp. 316-317, pp. 320-321.

Rane et al., "Membrane Filtration of Corn Steep Water", *Cereal Chemistry*, vol. 78, No. 4, (2001) pp. 400-404.

Reynolds, H., "Effect of type of Carbohydrate on Amino Acid Accumulation and Utilization by Tetrahymena", vol. 104, No. 2, (1970), pp. 719-725.

\* cited by examiner

FERMENTATIVE PRODUCTION OF ORGANIC COMPOUNDS

CROSS-REFERENCE TO RELATED APPLICATIONS

This application is a national stage application of PCT/EP2006/068926, filed Nov. 27, 2006, which claims priority of German Patent Application No. 102005056668.5, filed Nov. 28, 2005; the entire contents of all are hereby incorporated by reference.

The present invention relates to the fermentative production of organic compounds having at least 3 C atoms or having at least 2 C atoms and at least 1 N atom using, for culturing the microorganisms, a sugar-containing medium which comprises at least part of the nonstarchy solid constituents of the starch feedstock.

Sugar-containing liquid media are a basic nutrient source for a multiplicity of fermentative processes; the sugar components which are present in the media are metabolized by the microorganisms employed, giving rise to organic products of value. The range of microbial metabolites thus prepared, i.e. organic compounds, comprises for example low-molecular-weight volatile compounds such as ethanol, nonvolatile metabolites such as amino acids, vitamins and carotenoids, and a multiplicity of further substances.

Depending on the various process conditions, different carbon feedstocks are exploited for such generally known microbial fermentative processes. They extend from pure sucrose via beet, and sugarcane molasses to what are known as high-test molasses (inverted sugarcane molasses) to glucose from starch hydrolyzates. Moreover, acetic acid and ethanol are mentioned as cosubstrates which can be employed on an industrial scale for the biotechnological production of L-lysine (Pfefferle et al., Biotechnological Manufacture of Lysine, Advances in Biochemical Engineering/Biotechnology, Vol. 79 (2003), 59-112).

Based on the abovementioned carbon feedstocks, various methods and procedures for the sugar-based, fermentative production of microbial metabolites are established. Taking L-lysine as an example, these are described for example by Pfefferle et al. (loc. cit.) with regard to strain development, process development and industrial production.

An important carbon feedstock for the microorganism-mediated fermentative production of microbial metabolites is starch. The latter must first be liquefied and saccharified in preceding reaction steps before it can be exploited as carbon feedstock in a fermentation. To this end, the starch is usually obtained in pre-purified form from a natural starch feedstock such as potatoes, cassava, cereals, for example wheat, corn, barley, rye, triticale or rice, and subsequently enzymatically liquefied and saccharified, where after it is employed in the actual fermentation for producing the desired metabolites.

In addition to the use of such pre-purified starch feedstocks, the use of non-pretreated starch feedstocks for the preparation of carbon feedstocks for the fermentative production of microbial metabolites has also been described. Typically, the starch feedstocks are initially comminuted by grinding. The millbase is then subjected to liquefaction and saccharification. Since this millbase naturally comprises, besides starch, a series of nonstarchy constituents which may adversely affect the fermentation, these constituents are usually removed prior to fermentation. The removal can be effected either directly after grinding (WO 02/077252; JP 2001-072701; JP 56-169594; CN 1218111), after liquefaction (WO 02/077252; CN 1173541) or subsequently to saccharification (CN 1266102; Beukema et al.: Production of fermentation syrups by enzymatic hydrolysis of potatoes; potato saccharification to give culture medium (Conference Abstract), Symp. Biotechnol. Res. Neth. (1983), 6; NL8302229). However, all variants involve the use of a substantially pure starch hydrolyzate in the fermentation.

Novel processes for fermentative production of organic compounds comprise in particular a purification of the starch feedstocks prior to fermentation, for example the purification of liquefied and saccharified starch solutions (JP 57159500), or provide methods which are intended to make possible the preparation of fermentation media from renewable resources (EP 1205557).

Unprocessed starch feedstocks, in contrast, are known to be applied on a large scale in the fermentative production of bioethanol. Here, the starch feedstocks, usually whole cereal grains, are first subjected to dry milling, and the starch constituent of the starch feedstock is subsequently hydrolyzed using enzymes. Here, the hydrolysis can be carried out batchwise, for example in stirred vessels, or else continuously, for example in jet cookers. Descriptions of suitable processes can be found for example in "The Alcohol Textbook—A reference for the beverage, fuel and industrial alcohol industries", Jaques et al. (Ed.), Nottingham Univ. Press 1995, ISBN 1-8977676-735, Chapter 2, pp. 7 to 23, and in McAloon et al., "Determining the cost of producing ethanol from corn starch and lignocellulosic feedstocks", NREL/TP-580-28893, National Renewable Energy Laboratory, October 2000.

Since in the fermentative production of bioethanol the product of value is obtained by distillation, the use of starch feedstocks from the dry-milling process in non-prepurified form does not constitute a serious problem. However, when using a dry-milling method for the production of other microbial metabolites, the solids stream which is introduced into the fermentation via the sugar solution is problematic since it not only may have an adverse effect on the fermentation, for example regarding the oxygen transfer rate or the oxygen requirement of the microorganisms employed (cf., in this context, Mersmann, A. et al.: Selection and Design of Aerobic Bioreactors, Chem. Eng. Technol. 13 (1990), 357-370), but may also considerably complicate the subsequent workup.

Moreover, as a result of the introduction of solids, the viscosity of the suspension may reach a critical value even whilst the starch-containing suspension is being prepared, as a result of which for example a suspension containing more than 30% by weight of corn meal is no longer homogenously miscible in water (Industrial Enzymology, 2nd Ed., T. Godfrey, S. West, 1996). This limits the glucose concentration in traditional procedures. With regard to the fermentative production of bioethanol, this is no longer relevant in as far as higher concentrations can anyway not be converted in a meaningful manner as the result of the toxicity of the products to the yeasts employed for the fermentation.

Feeding to the fermentation sugar-containing media with a low sugar concentration is in principle disadvantageous in the fermentative production of organic metabolites other than ethanol because this procedure results in a disproportionate dilution of the fermentation liquor and, as a consequence, the achievable final concentration of the products of interest is reduced which firstly results in increased costs when these products are obtained from the fermentation medium and secondly the space-time yield decreases. These considerations are of importance in particular in the case where a starch hydrolyzate which is produced for a large-volume bioethanol production and which traditionally has low sugar or glucose concentrations of up to approximately 30 or 33% by weight is intended to be fed in part to a lower-volume secondary fermentation for the production of other chemicals.

Owing to these difficulties and limitations, dry-milling methods as they have been employed widely for the production of bioethanol have as yet remained without particular economical importance in the fermentative production of microbial metabolites other than ethanol.

To date, attempts to apply the dry-milling concept and the advantages which exist in principle in connection with this method, to the industrial-scale production of microbial metabolites have only been described using Cassava as starch feedstock. Thus, JP 2001/275693 describes a method for the fermentative production of amino acids in which peeled cassava tubers which have been ground in the dry state are employed as starch feedstock. It is necessary, in order to carry out the process, to adjust the particle size of the millbase to ≤150 μm. In the filtration step which is employed for this purpose, parts of the millbase, including non-starch-containing constituents, are removed before the starch present is liquefied/saccharified and subsequently fermented. In this process, moderate sugar concentrations are obtained. A similar process is described in JP 2001/309751 for the production of an amino-acid-containing feed additive.

Increased sugar concentrations in the liquid medium employed for the fermentation can be achieved by using a millbase, for the saccharification, which largely comprises the solid, nonstarchy constituent of the starch feedstock, by the process described in WO 2005/116228 (PCT/EP2005/005728) of the applicant company. Surprisingly, it has emerged that the solid, nonstarchy constituents which are present in the starch feedstock need not be removed before the fermentation. A similar process using starch feedstock selected among cereal grains is described in PCT/EP2006/066057 (earlier patent application DE 102005042541.0) of the applicant company. In some cases, inhibited or delayed multiplication of the microorganisms was observed.

It is an object of the present invention to provide another process for the fermentative production of organic compounds which requires no, at least no complete, previous removal of the nonstarchy solid constituents present in the starch feedstock. Moreover, it was to be distinguished by easy handling of the media used and by their unproblematic use in the fermentation process. In particular, the process was to allow the use of cereals as starch feedstock.

Surprisingly, it has now been found that the above problems of the prior art can be overcome by first preparing a first sugar-containing liquid medium (1) by milling, liquefying and saccharifying starch feedstocks without prior removal of the nonstarchy solid constituents of the starch feedstock and supplying a fermentation with this medium together with metabolizable mono-, di- or oligosaccharides or together with a composition which comprises metabolizable mono- or oligosaccharides in a concentration of at least 50% by weight and which is essentially free from solids which are insoluble in water.

The invention thus provides a process for the fermentative production of at least one organic compound having at least 3 C atoms or having at least 2 C atoms and at least one 1 N atom, comprising the following steps:

a1) milling a starch feedstock, thus obtaining a millbase which comprises at least part of the nonstarchy solid constituents of the starch feedstock;

a2) suspending the millbase in an aqueous liquid and hydrolysis of the starch portion in the millbase by enzymatic liquefaction and, if appropriate, subsequent saccharification, whereby a first liquid (1) which comprises mono- or oligosaccharides is obtained; and b) addition of liquid (1) which comprises mono- or oligosaccharides together with metabolizable mono-, di- or oligosaccharides or together with a composition which comprises metabolizable mono-, di- or oligosaccharides in a concentration of at least 50% by weight and which is essentially free from solids which are insoluble in water to a fermentation medium comprising a microorganism which is capable of overproducing the organic compound under fermentation conditions.

Using the liquid (1) which comprises mono- or oligosaccharides, which has been obtained by enzymatic hydrolysis, results in markedly reduced costs in the fermentative production of the organic compounds. The parallel addition of metabolizable sugars (i.e. the metabolizable mono-, di- or oligosaccharides) in concentrated form additionally avoids any undesired dilution of the fermentation liquor. Moreover, viscosity problems as they can arise upon liquefaction of the starch feedstock at higher millbase concentrations can be avoided as the result of the process according to the invention. Furthermore, problems with the multiplication of the microorganism can be avoided in this manner.

When referring to the liquid (1) which comprises mono- or oligosaccharides, the terms "liquid (1)" and "liquid medium (1)" will be used synonymously here and hereinbelow.

Suitable as starch feedstock for the process according to the invention are, mainly, dry cereals or seeds where the starch amounts to at least 40% by weight and preferably at least 50% by weight in the dried state. They are found in many of the cereal plants which are currently grown on a large scale, such as maize, wheat, oats, barley, rye, triticale, rice, sugar beet and potatoes and various sorghum and millet species, for example sorgo and milo. The starch feedstock is preferably selected from among cereal, especially preferably among maize, rye, triticale and wheat kernels. In principle, the process according to the invention can also be carried out with similar starch feedstocks such as, for example, a mixture of various starch-containing cereals or seeds.

To prepare the liquid medium (1), the starch feedstock in question is milled in step a1), with or without addition of liquid, for example water, preferably without addition of liquid. It is also possible to combine dry milling with a subsequent wet-milling step.

Apparatuses which are typically employed for dry milling are hammer mills, rotor mills or roller mills; those which are suitable for wet grinding are paddle mixers, agitated ball mills, circulation mills, disk mills, annular chamber mills, oscillatory mills or planetary mills. In principle, other mills are also suitable. The amount of liquid required for wet grinding can be determined by the skilled worker in routine experiments. It is usually adjusted in such a way that the dry matter content is in the range of from 10 to 20% by weight.

Milling brings about a particle size which is suitable for the subsequent process steps. In this context, it has proved advantageous when the millbase obtained in the milling step, in particular the dry milling step, in step a1) has flour particles, i.e. particulate constituents, with a particle size in the range of from 100 to 630 μm in an amount of from 30 to 100% by weight, preferably 40 to 95% by weight and especially preferably 50 to 90% by weight. Preferably, the millbase obtained comprises 50% by weight of flour particles with a particle size of more than 100 μm. As a rule, at least 95% by weight of the milled flour particles have a particle size of less than 2 mm. In this context, the particle size is measured by means of screen analysis using a vibration analyzer. In principle, a small particle size is advantageous for obtaining a high product yield. However, an unduly small particle size may result in problems, in particular problems due to clump formation/agglomeration, when the millbase is slurried during liquefaction or processing, for example during drying of the solids after the fermentation step.

Usually, flours are characterized by the extraction rate or by the flour grade, whose correlation with one another is such that the characteristic of the flour grade increases with increasing extraction rate. The extraction rate corresponds to the amount by weight of the flour obtained based on 100 parts by weight of millbase applied. While, during the milling process, pure, ultrafine flour, for example from the interior of the cereal kernel, is initially obtained, with further milling, i.e. with increasing extraction rate the amount of crude fiber and husk content in the flour increases and the starch content decreases. The extraction rate is therefore also reflected in what is known as the flour grade, which is used as a figure for classifying flours, in particular cereal flours, and which is based on the ash content of the flour (known as ash scale). The flour grade or type number indicates the amount of ash (minerals) in mg which is left behind when 100 g of flour solids are incinerated. In the case of cereal flours, a higher type number means a higher extraction rate since the core of the cereal kernel comprises approximately 0.4% by weight of ash, while the husk comprises approximately 5% by weight of ash. In the case of a lower extraction rate, the cereal flours thus consist predominantly of the comminuted endosperm, i.e. the starch content of the cereal kernels; in the case of a higher extraction rate, the cereal flours also comprise the comminuted, protein-containing aleurone layer of the grains; in the case of coarse meal, they also comprise the constituents of the protein-containing and fat-containing embryo and of the seed husks, which comprise raw fiber and ash. For the purposes of the invention, flours with a high extraction rate, or a high type number, are preferred in principle. If cereal is employed as starch feedstock, it is preferred that the intact kernels together with their husks are milled and processed, if appropriate after mechanical removal of the embryo and the husks beforehand.

In accordance with the invention, the millbase used for the preparation of the liquid medium (1) comprises at least some, preferably at least 20% by weight, in particular at least 50% by weight, specifically at least 90% by weight and very specifically at least 99% by weight of the nonstarchy solid constituents which are present in the milled cereal kernels, corresponding to the extraction rate. Based on the starchy constituents of the millbase (and thus on the amount of mono-, di- or oligosaccharide in the liquid medium (1)), the nonstarchy solid constituents in the millbase preferably amount to at least 10% by weight and in particular at least 15% by weight, for example from 15 to 75% by weight and specifically in the range of from 20 to 60% by weight.

The enzymatic hydrolysis of the millbase in accordance with step a2) can be carried out by customary methods known to the skilled worker, for example following the methods described in "The Alcohol Textbook—A reference for the beverage, fuel and industrial alcohol industries", Chapter 2, p. 7 to 23, which has been cited at the outset.

To this end, the millbase will first be mixed with an aqueous liquid, for example fresh water, recirculated process water, for example from subsequent fermentation, or with a mixture of these liquids, giving an aqueous suspension. This procedure is frequently also referred to as slurrying.

As a rule, the amount of millbase and aqueous liquid are chosen in such a way that hydrolysis gives an aqueous liquid medium (1) in which the total mono- di- and/or oligosaccharide concentration is in the range of from 100 to 750 g/kg, preferably in the range of from 150 to 700 g/kg and in particular in the range from 200 to 650 g/kg. Accordingly, the millbase is typically employed in an amount of from 150 to 800 g/kg, frequently in the range of from 200 to 750 g/kg and in particular in the range of from 250 to 700 g/kg, based on the total weight of the suspension (slurry).

In a preferred embodiment of the invention, the amount of millbase and aqueous liquid is chosen in such a way that hydrolysis gives an aqueous liquid medium (1) in which the total mono-, di- and/or oligosaccharide concentration is in the range of from 100 to 400 g/kg, preferably in the range of from 150 to 350 g/kg and in particular in the range from 200 to 300 g/kg. Accordingly, the millbase is typically employed in an amount of from 150 to 550 g/kg, frequently in the range of from 200 to 500 g/kg and in particular in the range of from 250 to 450 g/kg, based on the total weight of the suspension (slurry). In principle, it is also possible to employ greater amounts of millbase in order to achieve higher total mono-, di- and/or oligosaccharide concentrations, for example concentrations of above 400 g/kg to 700 g/kg, in particular in the range of from 450 to 650 g/kg or 500 g/kg to 650 g/kg.

For the enzymatic hydrolysis of the starch portion of the millbase, the millbase will, as a rule, first be liquefied in the presence of a starch-liquefying enzyme, as a rule an α-amylase. Other enzymes which are active under the reaction conditions and liquefied stable starch can also be employed.

To liquefy the starch present in the millbase, it is possible, in principle, to employ all liquefying enzymes, in particular α-amylases (enzyme class EC 3.2.1.1), for example α-amylases which have been obtained from *Bacillus lichenformis* or *Bacillus staerothermophilus*, specifically those which are used for liquefying materials, obtained by dry-milling methods, for the purposes of bioethanol production. The α-amylases which are suitable for liquefaction are also commercially available, for example from Novozymes under the name Termamyl 120 L, type L; or from Genencor under the name Spezyme. A combination of different α-amylases may also be employed for the liquefaction.

This gives a liquid medium which comprises the liquefied starch portion from the millbase, typically oligosaccharides with, as a rule, 3 to 18, in particular 6 to 12, monosaccharide units, in particular glucose units, and the nonstarchy constituents of the millbase employed, in particular the solid, nonstarchy constituents of the millbase employed for the liquefaction.

The amounts of starch-liquefying enzyme and millbase will advantageously be chosen in such a way that the viscosity during the gelling process is sufficiently reduced to make possible an efficient mixing of the suspension, for example by means of stirring. The viscosity of the reaction mixture during the gelling process is preferably not more than 20 Pas, especially preferably not more than 15 Pas and very especially preferably not more than 8 Pas. As a rule, the viscosity is measured using a Haake Viskosimeter type Roto Visko RV20 equipped with an M5 measuring system and an MVDIN instrumentation, at a temperature of 50° C. and a shear rate of 200 $s^{-1}$.

The α-amylase (or the starch-liquefying enzyme used) can initially be introduced into the reaction vessel or else added during step a2). Preferably, a part of the α-amylase required in step a2) is added at the beginning of step a2), or this part is initially introduced into the reactor. The total amount of α-amylase is usually in the range of from 0.002 to 3.0% by weight, preferably of from 0.01 to 1.5% by weight and especially preferably from 0.02 to 0.5% by weight, based on the total amount of starch feedstock employed.

The liquefaction can be carried out above or below the gelling temperature. Preferably, the liquefaction in step a2) is carried out at least in part above the gelling temperature, or gelatinization temperature, of the starch employed (known as the cooking process). The temperature required for the starch in question is known to the skilled worker (see "The Alcohol Textbook—A reference for the beverage, fuel and industrial alcohol industries", which has been cited at the outset, Chapter 2, p. 11) or can be determined by him by routine experimentation. As a rule, the temperature chosen is in the range of between 80 and 165° C., preferably between 90 and 150° C. and especially preferably in the range of from 100 to 140° C., the temperature, as a rule, being at least 5 K, in particular at least 10 K and especially preferably at least 20 K, for example 10 to 100 K, in particular 20 to 80 K, above the gelling temperature. At these temperatures, the granular structure of the starch is destroyed (gelling), making the enzymatic degradation of the latter possible.

For α-amylase (or the starch-liquefying enzyme used) to be optimally effective, step a2) is preferably carried out at least for some time at the pH optimum of the liquefying enzyme, frequently at a pH in the weakly acidic range, preferably between 4.0 and 7.0, especially between 5.0 to 6.5, the pH adjustment usually being carried out before or at the beginning of step a2); it is preferred to check and, if appropriate, readjust this pH during the liquefaction process. The pH is preferably adjusted using dilute mineral acids such as $H_2SO_4$ or $H_3PO_4$ or dilute aqueous alkali hydroxide solution such as NaOH or KOH.

In a preferred embodiment for liquefying the starch portion in the millbase in step a2), at least some of the millbase is added continuously or batchwise to the aqueous liquid. Preferably, at least 40% by weight, in particular at least 50% by weight and very especially preferably at least 55% by weight are added during the course of the liquefaction process to the reactor, but before any saccharification takes place. Frequently, the added amount will not exceed 90% by weight, in particular 85% by weight and especially preferably 80% by weight. Preferably, the portion of millbase which is added in the course of the process is fed into the reactor under conditions as are prevailing during the liquefaction phase. The addition can be effected batchwise, i.e. portionwise, in several portions, which amount to preferably in each case not more than 30% by weight, especially preferably not more than 20% by weight, for example 1 to 30% by weight and in particular 2 to 20% by weight of the total amount of the millbase to be liquefied, or else continuously. An essential aspect of this embodiment is that only some of the millbase, preferably not more than 60% by weight, in particular not more than 50% by weight and especially preferably not more than 45% by weight of the millbase is present in the reactor at the beginning of the liquefaction, while the remainder of the millbase is added during the liquefaction phase.

The liquefaction can also be carried out continuously, for example in a multi-step reaction cascade.

In a preferred embodiment, step a2) of the process according to the invention is carried out in such a way that a portion amounting to not more than 60% by weight, preferably not more than 50% by weight and especially preferably not more than 45% by weight, for example 10 to 60% by weight, in particular 15 to 50% by weight, and especially preferably 20 to 45% by weight, based on the total amount of millbase, is initially suspended in the aqueous liquid, and the liquefaction is subsequently carried out.

In a preferred embodiment, the discontinuous or continuous addition, in particular the portionwise addition, of some of the millbase in step a2) is carried out in such a way that the viscosity of the liquid medium is not more than 20 Pas, preferably not more than 15 Pas and especially preferably not more than 8 Pas. To aid the control of the viscosity, it has proved advantageous to add at least 25% by weight, preferably at least 35% by weight and especially preferably at least 50% by weight of the total amount of the added millbase at a temperature above the gelatinization temperature of the starch present in the millbase. Moreover, controlling the viscosity can furthermore be influenced by adding the at least one starch-liquefying enzyme, preferably an α-amylase, and/or the at least one saccharifying enzyme, preferably a glucoamylase, portionwise themselves.

To carry out the method according to the invention, it is possible to preheat the aqueous liquid used for suspending the solid millbase at a moderately increased temperature, for example in the range of from 40 to 60° C. However, it is preferred to employ the liquids at room temperature.

Then, the at least one starch-liquefying enzyme, preferably an α-amylase, is added to this suspension of the millbase. If some of the millbase is added only during the liquefaction phase, it is advantageous at the beginning only to add some of the α-amylase, for example 10 to 70% by weight, in particular 20 to 65% by weight, based on all of the α-amylase employed in step a2). The amount of α-amylase added at this point in time depends on the activity of the α-amylase in question under the reaction conditions with regard to the starch feedstock used and is generally in the range of from 0.0004 to 2.0% by weight, preferably from 0.001 to 1.0% by weight and especially preferably from 0.02 to 0.3% by weight, based on the total amount of the starch feedstock employed. As an alternative, the α-amylase portion can be mixed with the liquid used before the suspension is made.

The amount or portion of α-amylase employed is preferably added to the suspension before heating to the temperature used for the liquefaction has started, in particular at room temperature or only moderately increased temperature, for example in the range of from 20 to 30° C.

The suspension thus made is then heated, preferably at a temperature above the gelling temperature of the starch used. As a rule, a temperature in the range of between 80 and 165° C., preferably between 90 and 150° C. and especially preferably between 100 and 140° C. is chosen, the temperature preferably being at least 5 K, in particular 10 K and especially preferably at least 20 K, for example 10 to 100 K, in particular 20 to 80 K above the gelling temperature (gelatinization temperature). While monitoring the viscosity, further portions of the starch feedstock, for example in each case 1 to 30% by weight and in particular from 2 to 20% by weight, based on all of the millbase employed, are added gradually to the starch-containing suspension. It is preferred to add the portion of the millbase to be added in the course of the liquefaction step in at least 2, preferably at least 4 and especially preferably at least 6 fractions to the reaction mixture. As an alternative, the portion of the millbase which has not been employed for making the suspension can be added continuously during the liquefaction step in this embodiment. During the addition, the temperature should advantageously be kept above the gelling temperature of the starch.

After the desired temperature has been reached, or, if appropriate, after all of the flour has been added, the reaction mixture is usually maintained for some time, for example for 10 to 60 minutes or longer, if required, at the temperature set above the gelling temperature of the starch, i.e. cooked. Then, as a rule, the reaction mixture is cooled to a slightly lower temperature, but preferably above the gelling temperature, for example to 70 to 90° C. Thereafter, if appropriate, a further portion of α-amylase, preferably the largest portion, is added. In this case, the amount of α-amylase added at this point in time is, depending on the activity under the reaction conditions of the α-amylase used, preferably from 0.002 to 2.0% by weight, especially preferably from 0.01 to 1.0% by weight and very especially preferably from 0.02 to 0.4% by weight, based on the total amount of the starch feedstock employed.

To fully degrade the starch into dextrins, the reaction mixture is held at the set temperature, or, if appropriate, heated further, until the detection of starch by means of iodine or, if appropriate, another test for detecting starch is negative or at least essentially negative. If appropriate, one or more further α-amylase portions, for example in the range of from 0.001 to 0.5% by weight and preferably from 0.002 to 0.2% by weight, based on the total amount of the starch feedstock employed, may now be added to the reaction mixture.

Alternatively, it is possible, to liquefy the starch portion, first to heat the aqueous suspension comprising the millbase to a temperature above the gelatinization temperature of the starch present in the starch feedstock or the millbase by means of introducing steam. Typically, the suspension will be heated at a temperature which is at least 10 K and in particular at least 20 K, for example 10 to 100 K, in particular 20 to 80 K, above the gelatinization temperature in question. In particular, the suspension is heated to temperatures in the range of from 90 to 150° C., specifically in the range of from 100 to 140° C.

The steam employed for heating the suspension is typically superheated steam with a temperature of at least 105° C., in particular at least 110° C., for example 110 to 210° C. The steam is preferably introduced into the suspension at superatmospheric pressure. Accordingly, the steam preferably has a pressure of at least 1.5 bar, for example 1.5 to 16 bar, in particular 2 to 12 bar.

As a rule, steam is introduced into the suspension in such a way that the steam is introduced into the suspension at superatmospheric pressure, preferably a superatmospheric pressure of 1 to 10 or 11 bar, in particular 1.5 to 5 bar, preferably at high speed. The result of introducing the steam is that the suspension is instantly heated to temperatures of above 90° C., that is temperatures above the gelatinization temperature.

Heating with steam is preferably carried out in a continuously operating device which is charged with the suspension continuously at a specific feed pressure which is the result of the viscosity of the suspension, the feed rate and the geometry of the device and which, in the suspension charge zone, is charged with the hot steam via an adjustable nozzle at elevated pressure based on the feed pressure. Feeding the steam at elevated pressure means that not only is the suspension heated, but also mechanical energy is introduced into the system, and this mechanical energy promotes a further comminution of the millbase particles, brings about a particularly uniform energy supply, and thus brings about especially uniform gelatinization of the granular starch particles in the millbase. These devices typically have a tubular geometry. The steam is preferably fed in along the longitudinal axis of the tubular device. As a rule, the suspension is supplied at an angle of at least 45° or at a right angle. The adjustable nozzle typically has a conical geometry which tapers in the flow direction of the steam. A needle, or a cone which is arranged on a longitudinally displaceable rod, is arranged within this nozzle. Needle, or cone, together with the cone of the nozzle, forms an aperture. By displacing the needle, or the rod, longitudinally, the size of the aperture, and thus the cross-sectional area of the nozzle end can be adjusted in a simple manner, whereby the speed at which steam is supplied can be controlled in a simple manner.

These devices are typically also equipped with a mixing tube into which the suspension is transported after the steam has been supplied and in which the suspension leaves the device. This mixing tube is usually arranged along the steam supply and perpendicular to the feed. The mixing tube and the nozzle together typically form an aperture through which the suspension is transported. As the result of this aperture, additional shear forces act on the suspension during the transport process and thus increase the supply of mechanical energy to the suspension. The mixing tube can be arranged in such a way that it is longitudinally displaceable. Displacing the mixing tube is a simple way of adjusting the size of the aperture and thus of the drop of pressure in the device.

Such devices are known from the prior art under the name jet cooker, for example the device which is shown in "The Alcohol Textbook", Chapter 2, loc. cit., FIG. 13, and commercially available, for example under the name HYDRO-HEATER® from Hydro Thermal Corp. Waukesha Wis., USA.

When reaction is carried out continuously, the suspension treated with steam is, as a rule, subsequently transferred into an after-reaction zone in order to continue the gelling of the starch constituents. Typically, a superatmospheric pressure, typically an absolute pressure of in the range of from 2 to 8 bar, prevails in the after-reaction zone. The temperatures in the after-reaction zone are typically in the range of from 90 to 150° C. The residence time in this after-reaction zone can be in the range of from 1 minute to 4 hours, depending on the temperature of the suspension. The after-reaction zones typically have a tubular or column geometry. In one embodiment, the after-reaction zone has the geometry of a vertically arranged column. Here, the suspension, once it has left the steam treatment device, is applied in the upper zone of the column and withdrawn in the lower zone. In another embodiment of the invention, the after-reaction zone has a tubular geometry.

After the suspension has left the after-reaction zone, the pressure is released, as a rule, and a liquefaction is subsequently carried out. Releasing the pressure is preferably carried out in the form of a flash evaporation in order to cool the suspension to, preferably, temperatures of below 100° C., in particular below 85° C. As a rule, the starch thus disintegrated is then liquefied in a separate reaction vessel. The liquefaction can be carried out as described above.

In a preferred embodiment of the invention, at least some or all, generally at least 50%, in particular at least 80%, or else all of the starch-liquefying enzyme is added to the suspension of the millbase in the aqueous liquid before the steam heating process. In this manner, the liquefaction process already takes place while the mixture is heated to temperatures of above the gelatinization temperature. Heating with steam, and the after reaction phase, are carried out appropriately. A subsequent liquefaction step in a separate reaction vessel can be dispensed with. However, such a liquefaction step will preferably be carried out to complete the degradation of the starch into dextrins.

To stabilize the enzymes employed, the concentration of $Ca^{2+}$ ions may, if appropriate, be adjusted to an enzyme-specific optimum value, for example using $CaCl_2$. Suitable concentration values can be determined by the skilled worker in routine experiments. If, for example Termamyl is employed as α-amylase, it is advantageous to adjust the $Ca^{2+}$ concentration to, for example, 10 to 100 ppm, preferably 20 to 80 ppm and especially preferably approximately 30 to 70 ppm in the liquid medium, the unit ppm being based on weight and meaning g/1000 kg.

To fully degrade the starch into dextrins, the reaction mixture is held at the set temperature until the detection of starch by means of iodine or, if appropriate, another test for detecting starch is negative or at least essentially negative. If appropriate, one or more further α-amylase portions, for example in the range of from 0.001 to 0.5% by weight and preferably from 0.002 to 0.2% by weight, based on the total amount of the starch feedstock employed, may now be added to the reaction mixture.

This gives an aqueous starch hydrolyzate which comprises the liquefied starch portion from the millbase, typically dextrins and, if appropriate, further oligosaccharides and mono- or disaccharides, and the nonstarchy constituents of the millbase, in particular the solid, nonstarchy components of the millbase employed for the liquefaction.

After the starch liquefaction has ended, the dextrins present in the liquid medium can be saccharified, i.e. broken down into glucose, either continuously or batchwise, in a manner known per se. The liquefied medium can be saccharified fully in a specific saccharification tank before being employed in, for example, a subsequent fermentation step.

In a first embodiment of the invention, only a partial saccharification is carried out before the subsequent fermentation. For example, a procedure may be followed in which some of the dextrins present in the liquid medium, for example in the range of from 10 to 90% by weight and in particular in the range of from 20 to 80% by weight, based on the total weight of the dextrins (or of the original starch) is saccharified and the resulting sugar-containing liquid medium is employed in the fermentation. A further saccharification can then be effected in situ in the fermentation medium. Moreover, the saccharification can be carried out directly in the fermenter (in situ), dispensing with a separate saccharification tank.

Advantages of the in situ saccharification, i.e. of saccharification which is carried out in part or fully in the fermenter, are firstly a reduced investment outlay; secondly, a delayed release of the glucose may, if appropriate, allow to initially introduce a higher glucose concentration in the batch without inhibition or metabolic changes in the microorganisms employed taking place. In *E. coli*, for example, an unduly high glucose concentration leads to the formation of organic acids (acetate), while *Saccharomyces cerevisae* in such a case switches for example to fermentation, despite the presence of sufficient oxygen in aerated fermenters (Crabtree effect). A delayed release of glucose can be adjusted by controlling the glucoamylase concentration. This makes it possible to suppress the abovementioned effects, and more substrate can be introduced initially so that the dilution, which is the result of the feedstream supplied, can be reduced.

The saccharification of the dextrins (i.e. oligosaccharides) in the liquefied starch solution is carried out enzymatically, i.e. with the aid of at least one dextrin-saccharifying enzyme. Enzymes which can be used for this purpose are, in principle, all the glucoamylases (enzyme class EC 3.2.1.3), in particular glucoamylases obtained from *Aspergilus* and specifically those which are used for saccharifying materials obtained by dry-milling methods in connection with the production of bioethanol. The glucoamylases which are suitable for the saccharification are also commercially available, for example from Novozymes under the name Dextrozyme GA; or from Genencor under the name Optidex. A combination of different glucoamylases may also be used.

The at least one saccharifying enzyme, in particular at least one glucoamylase, is added to the dextrin-containing liquid medium obtained after the liquefaction in an amount of from usually 0.001 to 5.0% by weight, preferably 0.005 to 3.0% by weight and especially preferably 0.01 to 1.0% by weight, based on the total amount of the starch feedstock employed.

If the saccharification is carried out in the fermenter, the liquefied starch solution will, as a rule, be cooled to fermentation temperature, i.e. 32 to 37° C., before it is fed into the fermenter. In this case, the glucoamylase (or the at least one saccharifying enzyme) for the saccharification is added directly to the fermentation liquor. The saccharification of the liquefied starch in accordance with step a2) now takes place in parallel with the metabolization of the sugar by the microorganisms.

If the saccharification takes place in a saccharification tank, the liquefied starch solution is usually cooled or warmed to the temperature optimum of the saccharifying enzyme or slightly below, for example to 50 to 70° C., preferably 60 to 65° C., and subsequently treated with glucoamylase.

It is advantageous prior to adding the saccharifying enzyme, in particular the glucoamylase, to adjust the pH of the liquid medium to a value in the optimal activity range of the glucoamylase employed, preferably in the range of between 3.5 and 6.0; especially preferably between 4.0 and 5.5 and very especially preferably between 4.0 and 5.0. However, in particular when carrying out the saccharification directly in the fermenter, it is also possible to adjust the pH to a value outside the abovementioned ranges, for example in the range of from above 6.0 to 8.0. This may be overall advantageous for example in the fermentative production of lysine, pantothenate and vitamin $B_2$ despite the limited activity of standard glucoamylases in this pH range or necessary as the result of the fermentation conditions to be set.

In a preferred embodiment, the saccharification is carried out in a specific saccharification tank. To this end, the liquefied starch solution is warmed to a temperature which is optimal for the enzyme, or slightly below, and the pH is adjusted in the above-described manner to a value which is optimal for the enzyme.

After addition of the saccharifying enzyme, the dextrin-containing suspension is preferably held at the temperature set for a period of, for example, from 2 to 72 hours or longer, if required, in particular from 5 to 48 hours, during which time the dextrins are saccharified to give monosaccharides. The progress of the saccharification process can be monitored by the skilled worker using known methods, for example HPLC, enzyme assays or glucose test strips. The saccharification has ended when the monosaccharide concentration no longer arises substantially or drops again.

Since, as a rule, millbase which comprises at least some or all constituents of the starch feedstock is employed for the preparation of the sugar-containing liquid medium (1) (i.e. the nonstarchy solid constituents of the starch feedstock are not removed, or not fully removed), the liquid medium (1) obtained also comprises some or all of the nonstarchy solid constituents of the starch feedstock. This frequently brings about the introduction of an amount of phytate, for example from the cereal, which amount is not to be overlooked. To avoid the inhibitory effect which thus results, it is advantageous to add, in step a2), at least one phytase to the liquid medium before subjecting the sugar-containing liquid medium to a fermentation step.

The phytase can be added before, during or after the liquefaction or the saccharification, if it is sufficiently stable to the respective high temperatures.

Any phytases can be employed as long as their activity is in each case not more than marginally affected under the reaction conditions. Phytases used preferably have a heat stability (T50)>50° C. and especially preferably >60° C.

The amount of phytase is usually from 1 to 10000 units/kg starch feedstock and in particular 10 to 4000 units/kg starch feedstock.

To increase the overall sugar yield, or to obtain free amino acids, further enzymes, for example pullulanases, cellulases, hemicellulases, glucanases, xylanases, glucosidases or proteases, may additionally be added to the reaction mixture during the production of the sugar-containing liquid medium. The addition of these enzymes can have a positive effect on the viscosity, i.e. reduced viscosity (for example by cleaving long-chain (also referred to as longer-chain) glucans and/or (arabino-)xylans), and bring about the liberation of metabolizable glucosides and the liberation of (residual) starch. The use of proteases has analogous positive effects, it additionally being possible to liberate amino acids which act as growth factors for the fermentation.

Depending on whether a saccharification has been carried out or not, the application of steps a1) and a2) described herein result in a liquid medium which comprises dextrin- or mono- or disaccharide and which has a total mono-, di- and/or oligosaccharide concentration in the abovementioned ranges.

The sugars which are present in the liquid medium (1) after the saccharification are, in particular, glucose, with the presence of further monosaccharides such as hexoses and pentoses other than glucose, for example fructose, mannose, galactose, sorbose, xylose, arabinose and ribose, also being possible. The amount of monosaccharides other than glucose can depend on the starch feedstock used and on the non-starchy constituents present therein and can be influenced by the process control, for example by breaking down cellulose constituents by addition of cellulases. The monosaccharides of the sugar-containing liquid medium preferably comprise a glucose content of at least 60% by weight, frequently at least 70% by weight, in particular at least 80% by weight and specifically at least 85% by weight, based on the total amount of sugar present in the sugar-containing liquid medium. The glucose content is usually in the range of from 75 to 99.9% by weight, in particular 80 to 99% by weight and specifically 85 to 97% by weight, based on the total amount of sugar present in the sugar-containing liquid medium. If no saccharification has been carried out, the amount of dextrins in the mono-, di- and oligosaccharides present in the medium (1) corresponds essentially to the amount of glucose.

If no saccharification has been carried out, the metabolizable glucose equivalents are essentially present in the form of oligosaccharides, in particular dextrins. The main constituent of these oligosaccharides, or dextrins, is typically glucose, it also being possible for the medium to comprise small amounts of mono- and/or disaccharides and oligosaccharide units consisting of other monosaccharide units. In such a case, the sugar-containing constituents in the liquid medium (1), i.e. the mono-, di- and oligosaccharides, typically comprise at least 60% by weight, frequently at least 70% by weight, in particular at least 80% by weight, specifically at least 90% by weight of oligosaccharides, in particular dextrins, i.e. the mono- and disaccharides amount to less than 40% by weight, frequently less than 30% by weight, in particular less than 20% by weight and specifically less than 10% by weight. The glucose which is present in free or bound form usually amounts to in the range of from 50 to 99% by weight, in particular from 75 to 97% by weight and specifically from 80 to 95% by weight of the glucose equivalents of the medium (1), based on the total amount of glucose equivalents.

In accordance with the invention, the subsequent fermentation is carried out using both the liquid medium (1) and a feedstock of metabolizable mono-, di- and/or oligosaccharides (hereinbelow also referred to as sugar feedstock) other than the liquid medium. The mono-, di- and/or oligosaccharides used for this purpose can be employed either as such or in the form of a composition which comprises metabolizable mono-, di- and/or oligosaccharides in a concentration of at least 50% by weight, preferably in a concentration of at least 60% by weight, based on the total weight of the medium, and which, in contrast to the aqueous liquid medium (1), is essentially free from solids which are insoluble in water.

The mono-, di- or oligosaccharides present in the sugar feedstock are preferably selected from among monosaccharides, usually hexoses and/or pentoses, for example glucose, fructose, mannose, galactose, sorbose, xylose, arabinose and ribose, specifically among glucose, fructose and galactose, and disaccharides such as sucrose, maltose, lactose, specifically sucrose. Also suitable are mixtures of monosaccharides and disaccharides, and oligosaccharides with a high proportion of incorporated glucose components, and mixtures of these with monosaccharides and/or disaccharides.

Examples of compositions which comprise metabolizable mono-, di- and/or oligosaccharides in a concentration of at least 50% by weight and which are essentially free from solids which are insoluble in water comprise glucose syrups, sucrose syrups, thick juices, maltose syrups, dextrin syrups, but also waste products from sugar production (molasses), in particular molasses from beet sugar production and molasses from cane sugar production.

Especially preferred are substances which comprise predominantly mono- and/or disaccharides, in particular glucose and/or sucrose, and mixtures which comprise glucose and/or sucrose and oligosaccharides with a high proportion of incorporated glucose components, for example, glucose, sucrose, glucose syrups, sucrose syrups, thick juices and melasses.

Like the liquid medium (1), the mono-, di- and/or oligosaccharides, and the compositions comprising them, can be employed not only for initially preparing the fermentation medium (batch phase), but also for feeding in during the fermentation if the latter is carried out in the form of a fed batch, or semicontinuously.

The total amount of mono-, di- and/or oligosaccharides introduced into the fermentation by addition of the liquid medium (1) preferably accounts for at least 40% by weight, in particular for at least 50% by weight, especially preferably for at least 60% by weight, for example 40 to 95% by weight, in particular 50 to 90% by weight and specifically 60 to 90% by weight, of the total amount of the mono-, di- and oligosaccharides introduced into the fermentation.

Liquid medium (1) and the mono-, di- and/or oligosaccharides, or the compositions comprising them, can be fed into the fermentation either separately to one another or else together.

In a preferred embodiment of the invention, liquid medium (1) and the mono-, di- and/or oligosaccharides, or the composition comprising them, are mixed with one another before being fed into the fermentation. Thus, when employing a liquid medium which, as a rule, has a low total mono-, di- and oligosaccharide concentration of from 100 to 400 g/kg, the total sugar content of the sugar-containing liquid medium (1) which is obtained after steps a1) and a2) is increased, preferably by at least 50 g/kg, in particular by at least 100 g/kg, specifically by at least 150 g/kg, for example by 50 to 300 g/kg, in particular by 100 to 250 g/kg and specifically by 120 to 200 g/kg, to account for more than 40% by weight, preferably for at least 45% by weight, in particular for at least 50% by weight and especially preferably for at least 55% by weight, based on the total weight.

After the addition of these sugar feedstocks to the liquid medium (1), the resulting liquid medium preferably has a dry-matter content in the range of from 45 to 80% by weight and especially preferably in the range of from 50 to 75% by weight or 55 to 75% by weight, based on the total weight. In this context, it is advantageous to control the viscosity of the liquid medium (1), for example by adjusting the temperature, so that maximal values of 20 Pas, especially preferably 15 Pas and very especially preferably 8 Pas are not exceeded.

In a preferred embodiment of the invention, the mono- and/or disaccharides are added to the first liquid medium (1) in the form of a glucose- or sucrose-comprising by-product from sugar production. Examples are the melasses which are generated in sugar production from cane sugar or in particular beet sugar.

In accordance with the invention, the liquid medium (1) which is prepared in steps a1) and a2), and the sugar feedstocks which differ therefrom, are fed into a fermentation, where they serve for the culture of microorganisms. In the fermentation, the microbial metabolites are produced by the microorganisms.

The fermentation can be carried out in the customary manner which is known to the skilled worker. To this end, the desired microorganism will, as a rule, be cultured in the liquid medium obtained by the method described herein.

The fermentation method can be carried out batchwise or else fed-batch-wise (including fed batch with intermediate harvests), the fed-batch process being preferred.

For example, the liquid medium (1) obtained by the method according to the invention or a conventional sugar feedstock, i.e. metabolizable mono-, di- and/or oligosaccharides or the composition which comprises metabolizable mono-, di- and/or oligosaccharides in a concentration of at least 50% by weight and which is typically essentially free from solids which are insoluble in water, or their mixture, can be inoculated with the desired microorganism, if appropriate after dilution with water and addition of customary media constituents such as buffers, nutrient salts, nitrogen feedstocks such as ammonium sulfate, urea and the like, complex nutrient media constituents, comprising amino acids such as yeast extracts, peptones, CSL and the like, and this microorganism can be multiplied under fermentation conditions until the microorganism concentration reaches the stationary state which is desired for the fermentation. Here, the sugar present in the liquid medium (1) is metabolized and the desired metabolite is formed (also known as batch process or batch phase).

When carrying out a fed-batch process, the fermentation process will then be continued by supplying further liquid medium (1) obtainable by the method according to the invention and the sugar source other than the liquid medium (1), in particular by supplying the liquid medium obtained by mixing the liquid medium (1) with the sugar feedstock other than the liquid medium (1), and the metabolite which is overproduced by the microorganism accumulates in the fermentation liquor, it being possible for the metabolite to be present both in the cells of the microorganism and in the aqueous phase of the fermentation medium.

The fermentation will preferably be carried out as a fed-batch process. For doing so, a procedure will be followed in which the microorganism is first multiplied using a sugar-containing liquid medium, for example using a liquid medium (1) or another sugar feedstock, until the desired microorganism concentration in the fermenter has been reached. Thereafter, the liquid medium (1) together with the further sugar feedstock, i.e. metabolizable mono-, di- and/or oligosaccharides or a medium which comprises metabolizable mono-, di- and/or oligosaccharides in a concentration of at least 50% by weight and which is essentially free from solids which are insoluble in water, are then fed into the fermenter. This maintains the fermentation process, and the metabolite which is overproduced by the microorganism accumulates in the fermentation liquor (see hereinabove). The volume ratio of sugar-containing liquid medium (1) which is fed in and the further sugar feedstock to the batch medium which was initially introduced and which comprises the microorganisms is generally in the range of from approximately 1:10 to 10:1 and preferably approximately 1:5 to 5:1 and specifically in the range of from 1:1 to 5:1. The sugar content in the fermentation liquor can be controlled in particular via the feed rate of the sugar-comprising liquid medium. As a rule, the feed rate will be adjusted in such a way that the monosaccharide content in the fermentation liquor is within the range of from >0% by weight to approximately 5% by weight and in particular does not exceed a value of 3% by weight.

The sugar-comprising liquid medium obtained in step a2), or its mixture with the further sugar feedstock, can, if appropriate, be sterilized before the fermentation, the microorganisms usually being destroyed by thermal or chemical methods. For this purpose, the sugar-comprising liquid medium is usually heated at temperatures of above 80° C. The destruction or lysis of the cells can take place immediately before the fermentation. To this end, all of the sugar-comprising liquid medium is subjected to lysis or destruction. This can be carried out by thermal, mechanical or chemical means.

The invention particularly relates to a process for the production of organic nonvolatile compounds having at least 3 C atoms or having at least 2 C atoms and at least 1 N atom. In this context, nonvolatile organic compounds are understood as meaning those compounds which cannot be recovered by distillation from the fermentation liquor without undergoing decomposition. As a rule, these compounds have a boiling point above the boiling point of water, frequently above 150° C. and in particular above 200° C. under atmospheric pressure. As a rule, they are compounds which are in the solid state under standard conditions (298 K, 101.3 kPa).

However, it is also possible to employ the sugar-comprising liquid medium according to the invention in a fermentation for the production of nonvolatile microbial metabolites which, under atmospheric pressure, have a melting point below the boiling point of water and/or an oily consistency.

The term nonvolatile microbial metabolites comprises in particular organic mono-, di- and tricarboxylic acids which preferably have 3 to 10 carbon atoms and which, if appropriate, have one or more, for example 1, 2, 3 or 4, hydroxyl groups attached to them, for example tartaric acid, itaconic acid, succinic acid, propionic acid, lactic acid, 3-hydroxypropionic acid, fumaric acid, maleic acid, 2,5-furandicarboxylic acid, glutaric acid, levulic acid, gluconic acid, aconitic acid and diaminopimelic acid, citric acid; proteinogenic and non-proteinogenic amino acids, for example lysine, glutamate, methionine, phenylalanine, aspartic acid, tryptophan and threonine; purine and pyrimidine bases; nucleosides and nucleotides, for example nicotinamide adenine dinucleotide (NAD) and adenosine-5'-monophosphate (AMP); lipids; saturated and unsaturated fatty acids having preferably 10 to 22 carbon atoms, for example γ-linolenic acid, dihomo-γ-linolenic acid, arachidonic acid, eicosapentaenoic acid and docosahexaenoic acid; diols having preferably 3 to 8 carbon atoms, for example propanediol and butanediol; polyhydric alcohols (also referred to as alcohols with higher functionality) having 3 or more, for example 3, 4, 5 or 6, OH groups, for example glycerol, sorbitol, mannitol, xylitol and arabinitol; long-chain (also referred to as longer-chain) alcohols, having at least 4 carbon atoms, for example 4 to 22 carbon atoms, for example butanol; carbohydrates, for example hyaluronic acid and trehalose; aromatic compounds, for example aromatic amines, vanillin and indigo; vitamins and provitamins, for example ascorbic acid, vitamin $B_6$, vitamin $B_{12}$ and riboflavin, cofactors and what are known as nutraceuticals; proteins, for example enzymes such as amylases, pectinases, acid, hybrid or neutral cellulases, esterases such as lipases, pancreases, proteases, xylanases and oxidoreductases such as laccase, catalase and peroxidase, glucanases, phytases; carotenoids, for example lycopene, β-carotene, astaxanthin, zeaxanthin and canthaxanthin; ketones having preferably 3 to 10 carbon atoms and, if appropriate, 1 or more hydroxyl groups, for example acetone and acetoin; lactones, for example γ-butyrolactone, cyclodextrins, biopolymers, for example polyhydroxyacetate, polyesters, for example polylactide, polysaccharides, polyisoprenoids, polyamides; and precursors and derivatives of the abovementioned compounds. Other compounds which are suitable as nonvolatile microbial metabolites are described by Gutcho in Chemicals by Fermentation, Noyes Data Corporation (1973), ISBN: 0818805086.

The term "cofactor" comprises nonproteinaceous compounds which are required for the occurrence of a normal enzyme activity. These compounds can be organic or inorganic; preferably, the cofactor molecules of the invention are organic. Examples of such molecules are NAD and nicotinamide adenine dinucleotide phosphate (NADP); the precursor of these cofactors is niacin.

The term "nutraceutical" comprises food additives which promote health in plants and animals, in particular humans. Examples of such molecules are vitamins, antioxidants and certain lipids, for example polyunsaturated fatty acids.

The metabolites produced are selected in particular among enzymes, amino acids, vitamins, disaccharides, aliphatic mono- and dicarboxylic acids having 3 to 10 C atoms, aliphatic hydroxycarboxylic acids having 3 to 10 C atoms, ketones having 3 to 10 C atoms, alkanols having 4 to 10 C atoms and alkanediols having 3 to 10 and in particular 3 to 8 C atoms.

It is clear to the skilled worker that the compounds thus produced fermentatively are obtained in each case in the enantiomeric form produced by the microorganisms employed (if different enantiomers exist). Thus, as a rule, the respective L-enantiomer is obtained in the case of amino acids.

The microorganisms employed in the fermentation depend in a manner known per se on the microbial metabolites in question, as specified in detail hereinbelow. They can be of natural origin or genetically modified. Examples of suitable microorganisms and fermentation processes are those given in Table A hereinbelow:

TABLE A

| Substances | Microorganism | Reference |
|---|---|---|
| Tartaric acid | Lactobacilli, (for example Lactobacillus delbrueckii) | Rehm, H.-J.: Biotechnology, Weinheim, VCH, 1980 and 1993-1995; Gutcho, Chemicals by Fermentation, Noyes Data Corporation (1973), |
| Itaconic acid | Aspergillus terreus, Aspergillus itaconicus | Jakubowska, in Smith and Pateman (Eds.), Genetics and Physiology of Aspergillus, London: Academic Press 1977; Miall, in Rose (Ed.), Economic Microbiology, Vol. 2, pp. 47-119, London: Academic Press 1978; U.S. Pat. 3,044,941 (1962). |
| Succinic acid | Actinobacillus sp. 130Z, Anaerobiospirillum succiniproducens, Actinobacillus succinogenes, E. coli | Int. J. Syst. Bacteriol. 26, 498-504 (1976); EP 249773 (1987), Inventors: Lemme and Datta; U.S. Pat. 5,504,004 (1996), Inventors: Guettler, Jain and Soni; Arch. Microbiol. 167, 332-342 (1997); Guettler MV, Rumler D, Jain MK., Actinobacillus succinogenes sp. nov., a novel succinic-acid-producing strain from the bovine rumen. Int J Syst Bacteriol. 1999 Jan; 49 Pt 1: 207-16; U.S. Pat. 5,723,322, U.S. Pat. 5,573,931, U.S. Pat. 5,521,075, WO99/06532, U.S. Pat. 5,869,301, U.S. Pat. 5,770,435 |
| Hydroxypropionic acid | Lactobacillus delbrückii, L. leichmannii or Sporolactobacillus inulinus | RÖMPP Online Version 2.2 |
| Propionic acid | Propionibacterium, for example P. arabinosum, P. schermanii, P. freudenreichii, Clostridium propionicum, | Rehm, H.-J.: Biotechnology, Weinheim, VCH, 1980 and 1993-1995; Gutcho, Chemicals by Fermentation, Noyes Data Corporation (1973), |
| Diaminopimelic acid | Corynebacterium glutamicum | Rehm, H.-J.: Biotechnology, Weinheim, VCH, 1980 and 1993-1995; Gutcho, Chemicals by Fermentation, Noyes Data Corporation (1973), |
| Citric acid | Aspergillus niger, Aspergillus wentii | Crit. Rev. Biotechnol. 3, 331-373 (1986); Food Biotechnol. 7, 221-234 (1993); 10, 13-27 (1996). |
| Aconitic acid | Aspergillus niger, Aspergillus wentii | Crit. Rev. Biotechnol. 3, 331-373 (1986); Food Biotechnol. 7, 221-234 (1993); 10, 13-27 (1996).; Rehm, H.-J.: Biotechnology, Weinheim, VCH, 1980 and 1993-1995; |
| Malic acid | Aspergilli, for example Aspergillus flavus, A. niger, A. oryzae, Corynebacterium | U.S. Pat. 3,063,910 |
| Gluconic acid | Aspergilli, for example A. niger | Gutcho, Chemicals by Fermentation, Noyes Data Corporation (1973), |
| Butyric acid | Clostridium (for example Clostridium | Rehm, H.-J.: Biotechnology, Weinheim, VCH, 1980 and 1993-1995; |

TABLE A-continued

| Substances | Microorganism | Reference |
|---|---|---|
| | *acetobutylicum*, *C. butyricum*) | |
| Lactic acid | *Lactobacillus*, for example *L. delbrückii*, *L. leichmannii*, | Rehm, H.-J.: Biotechnology, Weinheim, VCH, 1980 and 1993-1995; |
| Lysine | *Corynebacterium glutamicum* | Ikeda, M.: Amino Acid Production Process (2003), Adv. Biochem. Engin/Biotechnol 79, 1-35. |
| Glutamate | *Corynebacterium glutamicum* | Ikeda, M.: Amino Acid Production Process (2003), Adv. Biochem. Engin/Biotechnol 79, 1-35. |
| Methionine | *Corynebacterium glutamicum* | Ikeda, M.: Amino Acid Production Process (2003), Adv. Biochem. Engin/Biotechnol 79, 1-35. |
| Phenylalanine | *Corynebacterium glutamicum, E. coli* | Trends Biotechnol. 3, 64-68 (1985); J. Ferment. Bioeng. 70, 253-260 (1990). |
| Threonine | *E. coli* | Ikeda, M.: Amino Acid Production Process (2003), Adv. Biochem. Engin/Biotechnol 79, 1-35. |
| Aspartic acid | *E. coli* | Ikeda, M.: Amino Acid Production Process (2003), Adv. Biochem. Engin/Biotechnol 79, 1-35 and references cited therein, Gutcho, Chemicals by Fermentation, Noyes Data Corporation (1973) |
| Purine and pyrimidine bases | *Bacillus subtilis* | Rehm, H.-J.: Biotechnology, Weinheim, VCH, 1980 and 1993-1995; Gutcho, Chemicals by Fermentation, Noyes Data Corporation (1973), |
| Nicotinamide adenine dinucleotide (NAD) | *Bacillus subtilis* | Rehm, H.-J.: Biotechnology, Weinheim, VCH, 1980 and 1993-1995; Gutcho, Chemicals by Fermentation, Noyes Data Corporation (1973), |
| Adenosine-5'-monophosphate (AMP) | *Bacillus subtilis* | Rehm, H.-J.: Biotechnology, Weinheim, VCH, 1980 and 1993-1995; Gutcho, Chemicals by Fermentation, Noyes Data Corporation (1973), |
| γ-Linolenic acid | *Mucor, Mortiella, Aspergillus* spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by *Pythium irregulare* for Lipid Production. Master Thesis Lousiana State University, 31.10.2002 (URN etd-1111102-205855). |
| Dihomo-γ-linolenic acid | *Mortiella, Conidiobolus, Saprolegnia* spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by *Pythium irregulare* for Lipid Production. Master Thesis Lousiana State University, 31.10.2002 (URN etd-1111102-205855). |
| Arachidonic acid | *Mortiella, Phytium* spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by Pythium irregulare for Lipid Production. Master Thesis Lousiana State University, 31.10.2002 (URN etd-1111102-205855). |
| Eicosapentaenoic acid | *Mortiella, Phytium* spp., *Rhodopseudomonas, Shewanella* spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by *Pythium irregulare* for Lipid Production. Master Thesis Lousiana State University, 31.10.2002 (URN etd-1111102-205855). |
| Docosahexaenoic acid | *Thraustochytrium, Entomophthora* spp., *Rhodopseudomonas, Shewanella* spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by *Pythium irregulare* for Lipid Production. Master Thesis Lousiana State University, 31.10.2002 (URN etd-1111102-205855). |
| Propanediol | *E. coli* | DE 3924423, U.S. Pat. 4,40,379, WO 9635799, U.S. Pat. 5,164,309 |
| Butanediol | *Enterobacter aerogenes, Bacillus subtilis, Klebsiella oxytoca* | Rehm, H.-J.: Biotechnology, Weinheim, VCH, 1980 and 1993-1995; Gutcho, Chemicals by Fermentation, Noyes Data Corporation (1973), H. G. SCHLEGEL and H. W. JANNASCH, 1981; Afschar et al.: Mikrobielle Produktion von 2,3-Butandiol [Microbial production of 2,3-butane diol. CIT 64 (6), 2004, 570-571 |
| Butanol | *Clostridium* (e.g. *Clostridium acetobutylicum, C. propionicum*) | Rehm, H.-J.: Biotechnology, Weinheim, VCH, 1980 and 1993-1995; Gutcho, Chemicals by Fermentation, Noyes Data Corporation (1973), |
| Glycerol | Yeast, *Saccharomyces rouxii* | Gutcho, Chemicals by Fermentation, Noyes Data Corporation (1973), |

TABLE A-continued

| Substances | Microorganism | Reference |
|---|---|---|
| Mannitol | *Aspergillus candida*, *Torulopsis mannitofaciens* | Gutcho, Chemicals by Fermentation, Noyes Data Corporation (1973), |
| Arabitol | *Saccharomyces rouxii, S. mellis, Sclerotium glucanicum, Pichia ohmeri* | Gutcho, Chemicals by Fermentation, Noyes Data Corporation (1973), |
| Xylitol | *Saccharomyces cerevisiae* | Gutcho, Chemicals by Fermentation, Noyes Data Corporation (1973), |
| Hyaluronic acid | *Streptococcus* spp. | Rehm, H.-J.: Biotechnology, Weinheim, VCH, 1980 and 1993-1995; |
| Trehalose | *Brevibacterium, Corynebacterium, Microbacterium, Arthrobacter* spp., *Pleurotus* genus, *Filobasidium floriforme* | JP 05099974, JP 06311891, FR 2671099, EP 0555540, JP 3053791, Miyazaki, J.-I., Miyagawa, K.-I., Sugiyama, Y.: Trehalose Accumulation by Basidiomycotinous Yeast, *Filobasidium floriforme*. Journal of Fermentation and Bioengineering 81, (1996) 4, 315-319. |
| Ascorbic acid | *Gluconobacter melanogenes* | RÖMPP Online Version 2.2 |
| Vitamin $B_{12}$ | *Propionibacterium* spp., *Pseudomonas denitrificans* | Chem. Ber. 1994, 923-927; RÖMPP Online Version 2.2 |
| Riboflavin | *Bacillus subtilis, Ashbya gossypii* | WO 01/011052, DE 19840709, WO 98/29539, EP 1186664; Fujioka, K.: New biotechnology for riboflavin (vitamin B2) and character of this riboflavin. Fragrance Journal (2003), 31(3), 44-48. |
| Vitamin $B_6$ | *Rhizobium tropici, R. meliloti* | EP0765939 |
| Enzymes | *Aspergilli* (for example *Aspergillus niger A. oryzae*), *Trichoderma, E. coli, Hansenula* or *Pichia* (for example *Pichia pastorius*), *Bacillus* (for example *Bacillus licheniformis B. subtilis*) and many others | Rehm, H.-J.: Biotechnology, Weinheim, VCH, 1980 and 1993-1995; Gutcho, Chemicals by Fermentation, Noyes Data Corporation (1973), |
| Zeaxanthin | *Dunaliella salina* | Jin et al (2003) Biotech.Bioeng. 81: 115-124 |
| Canthaxanthin | *Brevibacterium* | Nelis et al (1991) J Appl Bacteriol 70: 181-191 |
| Lycopene | *Blakeslea trispora, Candida utilis* | WO 03/056028, EP 01/201762, WO 01/12832, WO 00/77234, Miura et al (1998) Appl Environ Microbiol 64: 1226-1229 |
| β-Carotene | *Blakeslea trispora, Candida utilis* | Kim S., Seo W., Park Y., Enhanced production of beta-carotene from *Blakeslea trispora* with Span 20, Biotechnology Letters, Vol 19, No 6, 1997, 561-562; Mantouridou F., Roukas T.: Effect of the aeration rate and agitation speed on beta-carotene production and morphology of *Blakeslea trispora* in a stirred tank reactor: mathematical modelling, Biochemical Engineering Journal 10 (2002), 123-135; WO 93/20183; WO 98/03480, Miura et al (1998) Appl Environ Microbiol 64: 1226-1229 |
| Astaxanthin | *Phaffia rhodozyma; Candida utilis* | US 5,599,711; WO 91/02060, Miura et al (1998) Appl Environ Microbiol 64: 1226-1229 |
| Polyhydroxy-alkanoates, polyesters | *Escherchia coli, Alcaligenes latus*, and many others | S. Y. Lee, Plastic Bacteria, Progress and Prospects for polyhydroxyalkanoate production in bacteria, Tibtech, Vol. 14, (1996), pp. 431-438., Steinbüchel, 2003; Steinbüchel (Ed.), Biopolymers, 1st ed., 2003, Wiley-VCH, Weinheim and references cited therein |
| Polysaccharides | *Leuconostoc mesenteroides, L. dextranicum, Xanthomonas campestris*, and many others | Rehm, H.-J.: Biotechnology, Weinheim, VCH, 1980 and 1993-1995; Gutcho, Chemicals by Fermentation, Noyes Data Corporation (1973), |
| Polyisoprenoids | *Lactarius* sp., *Hygrophorus* sp., *Russula* sp. | Steinbüchel (Ed.), Biopolymers, 1st ed., 2003, Wiley-VCH, Weinheim and references cited therein |
| Acetone | *Clostridium* (for example *Clostridium acetobutylicum, C. propionicum*) | Rehm, H.-J.: Biotechnology, Weinheim, VCH, 1980 and 1993-1995; Gutcho, Chemicals by Fermentation, Noyes Data Corporation (1973), |
| Acetoin | *Enterobacter aerogenes, Clostridium* | Lengeler, J. W., Drews, G., Schlegel, H. G.: Eds., Biology of the Procaryotes, Thieme, Stuttgart (1999), p. 307; RÖMPP Online-Edition |

TABLE A-continued

| Substances | Microorganism | Reference |
| --- | --- | --- |
| Vanillin | acetobutylicum, Lactococcus lactis Pseudomonas putida, Amycolatopsis sp. | Priefert, H., Rabenhorst, J., Seinbüchel, A. Biotechnological production of vanillin. Appl. Microbiol. Biotechnol. 56, 296-314 (2001) |
| Thuringensin | Bacillus thuringiensis | Jian-Zhong Jong et al.: Fed-batch culture of Bacillus thuringiensis for thuringensin production in a tower type bioreactor. Biotechnology and Bioengineering 48 (3) (2004), 207-213. |
| Polyketides | Streptomyces fradiae, Sorangium cellulosum | Kirst: Fermentation-derived compounds as a source for new products. Pure & Appl. Chem. 70 (2), (1998), 335-338; Zirkle et al.: Heterologous production of the antifungal polyketide antibiotic soraphen A of Sorangium cellulosum So ce26 in Streptomyces lividans. Microbiology 150 (8), (2004), 2761-74. |
| Gibberellic acid | Gibberella fujikuroi | Hollmann et al.: Extractive fermentation of Gibberellic acid using Gibberella fujikuroi. CIT 7 (1995), 892-895. |
| Indigo | Escherichia coli JB 102 | Berry, A., Dodge, T. C., Pepsin, M., Weyler, W.: Application of metabolic engineering to improve both the production and use of biotech indigo. Journal of Industrial Microbiology & Biotechnology 28 (2002), 127-133. |

In preferred embodiments of the invention, the organic compound which has been produced is selected among mono-, di- and tricarboxylic acids which optionally have hydroxyl groups attached to them and which have 3 to 10 C atoms, among proteinogenic and nonproteinogenic amino acids, purine bases, pyrimidine bases; nucleosides, nucleotides, lipids; saturated and unsaturated fatty acids; diols having 4 to 10 C atoms, polyhydric alcohols having 3 or more hydroxyl groups, long-chain alcohols having at least 4 C atoms, carbohydrates, aromatic compounds, vitamins, provitamins, cofactors, nutraceuticals, proteins, carotenoids, ketones having 3 to 10 C atoms, lactones, biopolymers and cyclodextrins.

A first preferred embodiment of the invention relates to the use of the sugar-comprising liquid medium which can be obtained in accordance with the invention in a fermentative production of enzymes such as phytases, xylanases or glucanases.

A second preferred embodiment of the invention relates to the use of the sugar-comprising liquid medium which can be obtained in accordance with the invention in a fermentative production of amino acids such as lysine, methionine, threonine.

A further preferred embodiment of the invention relates to the use of the sugar-comprising liquid medium which can be obtained in accordance with the invention in a fermentative production of vitamins such as pantothenic acid and riboflavin, and the precursors and derivatives.

Further preferred embodiments of the invention relate to the use of the sugar-comprising liquid medium which can be obtained in accordance with the invention in a fermentative production of mono-, di- and tricarboxylic acids, in particular aliphatic mono- and dicarboxylic acids having 3 to 10 C atoms, such as propionic acid, fumaric acid and succinic acid,
aliphatic hydroxycarboxylic acids having 3 to 10 C atoms, such as lactic acid;
long-chain alkanols as mentioned above, in particular alkanols having 4 to 10 C atoms, such as butanol;
diols as mentioned above, in particular alkanediols having 3 to 10, in particular 3 to 8, C atoms, such as propanediol;
ketones as mentioned above, in particular ketones having 3 to 10 C atoms, such as acetone; and
carbohydrates as mentioned above, in particular disaccharides such as trehalose.

In a further especially preferred embodiment, the metabolite produced by the microorganisms in the fermentation are polyhydroxyalkanoates such as poly-3-hydroxybutyrate and copolyesters with other organic hydroxycarboxylic acids such as 3-hydroxyvaleric acid, 4-hydroxybutyric acid and others which are described in Steinbüchel (loc. cit.), including for example long-chain (also referred to as longer-chain) hydroxycarboxylic acids such as 3-hydroxyoctanoic acid, 3-hydroxydecanoic acid and 3-hydroxytetradecanoic acid, and mixtures of these. To carry out the fermentation, analogous conditions and procedures as have been described for other carbon feedstocks, for example in S. Y. Lee, Plastic Bacteria Progress and prospects for polyhydroxyalkanoate production in bacteria, Tibtech, Vol. 14, (1996), pp. 431-438, may be employed.

In a preferred embodiment, the microorganisms which are employed in the fermentation are therefore selected among natural or recombinant microorganisms which overproduce at least one of the following metabolites:

enzymes such as phytase, xylanase or glucanase;
amino acids such as lysine, threonine or methionine;
vitamins such as pantothenic acid and riboflavin; and their precursors and/or derivatives;
disaccharides such as trehalose;
aliphatic mono- and dicarboxylic acids having 3 to 10 C atoms, such as propionic acid, fumaric acid and succinic acid;
aliphatic hydroxycarboxylic acids having 3 to 10 C atoms such as lactic acid;
polyhydroxyalkanoates such as poly-3-hydroxybutyrate and copolyesters of 3-hydroxybutyric acid;
ketones having 3 to 10 C atoms such as acetone;
alkanols having 4 to 10 C atoms such as butanol; and alkanediols having 3 to 8 C atoms such as propanediol.

Suitable microorganisms are usually selected among the genera Corynebacterium, Bacillus, Ashbya, Escherichia, Aspergillus, Alcaligenes, Actinobacillus, Anaerobiospirillum, Lactobacillus, Propionibacterium, Rhizopus and Clostridium, in particular among strains of Corynebacterium glutamicum, Bacillus subtilis, Ashbya gossypii, Escherichia coli, Aspergillus niger or Alcaligenes latus, Anaerobiospiril-

*lum succiniproducens, Actinobacillus succinogenes, Lactobacillus delbruckii, Lactobacillus leichmannii, Propionibacterium arabinosum, Propionibacterium schermanii, Propionibacterium freudenreichii, Clostridium propionicum, Clostridium formicoaceticum, Clostridium acetobutylicum, Rhizopus arrhizus* and *Rhizopus oryzae*.

In a preferred embodiment, the microorganism employed in the fermentation is a strain of the genus *Corynebacterium*, in particular a strain of *Corynebacterium glutamicum*. In particular, it is a strain of the genus *Corynebacterium*, specifically of *Corynebacterium glutamicum*, which overproduces an amino acid, specifically lysine, methionine or glutamate.

In a further preferred embodiment, the microorganism employed in the fermentation is a strain of the genus *Escherichia*, in particular a strain of *Escherichia coli*. In particular, it is a strain of the genus *Escherichia*, specifically of *Escherichia coli*, which overproduces an amino acid, specifically lysine, methionine or threonine.

In a specific preferred embodiment, the metabolite produced by the microorganisms in the fermentation is lysine. To carry out the fermentation, analogous conditions and procedures as have been described for other carbon feedstocks, for example in Pfefferle et al., loc. cit. and U.S. Pat. No. 3,708,395, can be employed. In principle, both a continuous and a discontinuous (batch or fed-batch) mode of operation are suitable, with the fed-batch mode being preferred.

In a further especially preferred embodiment, the metabolite produced by the microorganisms in the fermentation is methionine. To carry out the fermentation, analogous conditions and procedures as have been described for other carbon feedstocks, for example in WO 03/087386 and WO 03/100072, may be employed.

In a further especially preferred embodiment, the metabolite produced by the microorganisms in the fermentation is pantothenic acid. To carry out the fermentation, analogous conditions and procedures as have been described for other carbon feedstocks, for example in WO 01/021772, may be employed.

In a further especially preferred embodiment, the metabolite produced by the microorganisms in the fermentation is riboflavin. To carry out the fermentation, analogous conditions and procedures as have been described for other carbon feedstocks, for example in WO 01/011052, DE 19840709, WO 98/29539, EP 1 186 664 and Fujioka, K.: New biotechnology for riboflavin (vitamin B2) and character of this riboflavin. Fragrance Journal (2003), 31(3), 44-48, may be employed.

In a further especially preferred embodiment, the metabolite produced by the microorganisms in the fermentation is fumaric acid. To carry out the fermentation, analogous conditions and procedures as have been described for other carbon feedstocks, for example in Rhodes et al, Production of Fumaric Acid in 20-L Fermentors, Applied Microbiology, 1962, 10 (1), 9-15, may be employed.

In a further especially preferred embodiment, the metabolite produced by the microorganisms in the fermentation is succinic acid. To carry out the fermentation, analogous conditions and procedures as have been described for other carbon feedstocks, for example in Int. J. Syst. Bacteriol. 26, 498-504 (1976); EP 249773 (1987), to Lemme and Datta; U.S. Pat. No. 5,504,004 (1996), to Guettler, Jain and Soni; Arch. Microbiol. 167, 332-342 (1997); Guettler M V, Rumler D, Jain M K., Actinobacillus succinogenes sp. nov., a novel succinic-acid-producing strain from the bovine rumen. Int J Syst Bacteriol. 1999 January; 49 Pt 1:207-16; U.S. Pat. No. 5,723,322, U.S. Pat. No. 5,573,931, U.S. Pat. No. 5,521,075, WO99/06532, U.S. Pat. No. 5,869,301 or U.S. Pat. No. 5,770,435, may be employed.

In a further especially preferred embodiment, the metabolite produced by the microorganisms in the fermentation is a phytase. To carry out the fermentation, analogous conditions and procedures as have been described for other carbon feedstocks, for example in WO 98/55599, may be employed.

The fermentation generates a fermentation liquor which, in addition to the desired microbial metabolite, essentially comprises the biomass produced during the fermentation, the nonmetabolized constituents of the saccharified starch solution and, in particular, the nonstarchy solid constituents of the starch feedstock such as, for example, fibers and nonutilized sugars, and also nonutilized buffer and nutrient salts. In the present application, this liquid medium is also referred to as fermentation liquor, the term fermentation liquor also comprising the (sugar-comprising) liquid medium in which the sugars present have only been subjected to partial or incomplete fermentative conversion, i.e. in which a partial or incomplete microbial metabolization of the utilizable sugars (for example mono- and disaccharides) has taken place.

Before the isolation or depletion of a microbial metabolite or before the removal of the volatile constituents of the fermentation liquor, a sterilization step may be carried out in the above-described manner.

A specific embodiment of the invention relates to a process in which at least one microbial metabolite is depleted or isolated from the fermentation liquor. Most of the volatile constituents of the fermentation liquor are subsequently removed, giving rise to a solid or semisolid protein composition. A more detailed description for carrying out such a process, and of the protein composition obtained, is subject matter of WO 2005/116228 (PCT/EP2005/005728) of the applicant company, which is referred to with regard to further details.

The isolation or depletion of the metabolites from the fermentation liquor, i.e. the organic compound having at least 3 C atoms or having at least 2 C atoms and at least one N atom (hereinbelow also referred to as product of value) is usually carried out in such a way that at least one metabolite is depleted or isolated from the fermentation liquor so that the content of this metabolite in the fermentation liquor which remains amounts to not more than 20% by weight, in particular not more than 10% by weight, specifically not more than 5% by weight and very specifically not more than 2.5% by weight, in each case based on the total weight of the remaining fermentation liquor.

The microbial metabolite can be isolated or depleted from the fermentation liquor in one or more steps. An essential step in this context is the removal of the solid constituents from the fermentation liquor. This can be carried out either before or after isolation of the product of value. Methods conventionally used in the art which also comprise steps for the rough cleaning and the fine purification of the products of value and for formulation are known both for the isolation of products of value and for the removal of solids, i.e. solid-liquid phase separation (for example described in Belter, P. A, Bioseparations: Downstream Processing for Biotechnology, John Wiley & Sons (1988), and Ullmann's Encyclopedia of Industrial Chemistry, 5th ed. on CD-ROM, Wiley-VCH).

To isolate the product of value, a procedure can advantageously be followed in which the solid constituents are first removed from the fermentation liquor, for example by means of centrifugation or filtration, and the product of value is subsequently isolated from the liquid phase, for example by crystallization, precipitation, adsorption or distillation. As an alternative, the product of value can also be isolated directly from the fermentation liquor, for example by using chromatographic methods or extractive methods. A chromatographic method which must be mentioned in particular is ion-exchange chromatography, where the product of value can be isolated selectively on the chromatography column. In this case, the removal of the solids from the fermentation liquor which remains is advantageously carried out for example by decanting, evaporation and/or drying.

In the case of volatile or oily compounds, it is, as a rule, necessary to monitor the maximum temperatures during processing, in particular during drying. These compounds can advantageously also be prepared by formulating them in pseudo-solid form on adsorbents. Adsorbents which are suitable for this purpose are detailed for example in WO 2005/116228 (PCT/EP2005/005728) of the applicant company. Examples of compounds which can advantageously be prepared in this manner are γ-linolenic acid, dihomo-γ-linolenic acid, arachidonic acid, eicosapentaenoic acid and docosahexaenoic acid, furthermore propionic acid, lactic acid, propanediol, butanol and acetone. These compounds in pseudo-solid formulation are also understood as being, for the purposes of the present invention, nonvolatile microbial metabolites in solid form.

A further specific embodiment relates to a process in which the volatile constituents of the fermentation liquor are largely or fully removed, without previously isolating or depleting a nonvolatile microbial metabolite, and, if appropriate, without previously removing at least some solid constituents, giving rise to a solid formulation of a nonvolatile microbial metabolite. A more detailed description for carrying out such a process can be found in PCT/EP2006/066057 (earlier patent application DE 102005042541.0) of the applicant company.

"Largely" means that, once the volatile constituents have been removed, a solid or at least semisolid residue remains which can, if appropriate, be converted into solid product by addition of solids. As a rule, this means the removal of the volatile constituents down to a residual moisture content of not more than 30% by weight, frequently not more than 20% by weight and in particular not more than 15% by weight. As a rule, the volatile constituents of the fermentation liquor will advantageously be removed from the fermentation liquor down to a residual moisture content in the range of from 0.2 to 30% by weight, preferably 1 to 20% by weight, especially preferably 2 to 15% by weight and very especially preferably 5 to 15% by weight, based on the total weight of the solid constituents determined after drying. The residual moisture content can be determined by conventional methods with which the skilled worker is familiar, for example by means of thermogravimetry (Hemminger et al., Methoden der thermischen Analyse [Methods of thermal analysis], Springer Verlag, Berlin, Heidelberg, 1989).

Obtaining the nonvolatile metabolite(s) in solid form from the fermentation liquor can be effected in one, two or more steps, in particular in a one- or two-step procedure. As a rule, at least one step, in particular the final step, for obtaining the metabolite in solid form will comprise a drying step.

In the one-step procedure, the volatile constituents of the fermentation liquor will be removed, if appropriate after aforementioned preliminary removal, until the desired residual moisture content is reached.

In the two- or multi-step procedure, the fermentation liquor will first be concentrated, for example by filtration (microfiltration, ultrafiltration) or thermally by evaporating a part of the volatile constituents. The amount of volatile constituents which are removed in this step amounts, as a rule, to 10 to 80% by weight and in particular 20 to 70% by weight, based on the dry matter of the volatile constituents of the fermentation liquor. In one or more subsequent steps, the remaining volatile constituents of the fermentation liquor are removed until the desired residual moisture content has been reached.

In accordance with this embodiment, the volatile constituents are essentially removed from the liquid medium without previous depletion or indeed isolation of the product of value. As a consequence, when removing the volatile constituents of the fermentation liquor, the nonvolatile metabolite is essentially not removed together with the volatile constituents of the liquid medium, but remains in the resulting residue together with at least a part, usually with most and in particular with all of the other solid constituents from the fermentation liquor. Accordingly, however, it is also possible to remove—preferably small—amounts of the desired nonvolatile microbial metabolite, as a rule not more than 20% by weight, for example 0.1 to 20% by weight, preferably not more than 10, in particular not more than 5% by weight, especially preferably not more than 2.5% by weight and very especially preferably not more than 1% by weight, based on the total dry matter of the metabolite, together with the volatile constituents of the fermentation liquor when removing these constituents. In a very especially preferred embodiment, the desired nonvolatile microbial metabolite remains to at least 90% by weight, in particular at least 95% by weight, specifically 99% by weight and very specifically approximately 100% by weight, in each case based on the total dry weight of the metabolite, as solid in mixture with the portion of the solid constituents of the fermentation medium which has been obtained after removal of the volatile constituents, or with all of the solid constituents of the fermentation medium.

If desired, a portion, for example 5 to 80% by weight and in particular 30 to 70% by weight, of the nonstarchy solid constituents can be separated from the fermentation liquor, for example by means of centrifugation or filtration, before the volatile constituents are removed. If appropriate, such a preliminary separation will be carried out in order to remove coarser solids particles which comprise no, or only small amounts of, nonvolatile microbial metabolite. This preliminary filtering can be carried out using conventional methods which are known to the skilled worker, for example using coarse sieves, nets, perforated orifice plates or the like. If appropriate, coarse solids particles may also be separated off in a centrifugal-force separator. The equipment employed here, such as decanter, centrifuges, sedicanter and separators are also known to the skilled worker. In this manner, a solid or semisolid, for example pasty, residue is obtained which comprises the nonvolatile metabolite and the nonvolatile, generally solid, nonstarchy constituents of the starch feedstock or at least large portions thereof, frequently at least 90% by weight or all of the solid nonstarchy constituents.

The properties of the dry metabolite, which is present together with the solid constituents of the fermentation, can be formulated in a manner known per se specifically with regard to a variety of parameters such as active substance content, particle size, particle shape, tendency to dust, hygroscopicity, stability, in particular storage stability, color, odor, flowing behavior, tendency to agglomerate, electrostatic charge, sensitivity to light and temperature sensitivity, mechanical stability and redispersibility, by addition of formulation auxiliaries such as carrier and coating materials, binders and other additives.

The formulation auxiliaries which are conventionally used include, for example, binders, carrier materials, powdering/flow adjuvants, furthermore color pigments, biocides, dispersants, antifoams, viscosity regulators, acids, alkalis, antioxidants, enzyme stabilizers, enzyme inhibitors, adsorbates, fats, fatty acids, oils or mixtures of these. Such formulation auxiliaries are advantageously employed as drying aids in particular when using formulation and drying methods such as spray drying, fluidized-bed drying and freeze-drying. Further details can be found in PCT/EP2006/066057 (earlier application DE 102005042541.0).

The amount of the abovementioned additives and, if appropriate, further additives such as coating materials can vary greatly, depending on the specific requirements of the metabolite in question and on the properties of the additives employed and can be for example in the range of from 0.1 to 80% by weight and in particular in the range of from 1 to 30% by weight, in each case based on the total weight of the product or substance mixture in its finished formulated form.

The addition of formulation auxiliaries can be effected before, during or after working up the fermentation liquor (also referred to as product formulation or solids design), in particular during drying. An addition of formulation auxiliaries before working up the fermentation liquor or the metabolite can be advantageous in particular for improving the processibility of the substances or products to be worked up. The formulation auxiliaries can be added either to the metabolite obtained in solid form or else to a solution or suspension comprising the metabolite, for example directly to the fermentation liquor after the fermentation has been completed or to a solution or suspension obtained during work-up and before the final drying step.

Thus, for example, the auxiliaries can be admixed with a suspension of the microbial metabolite; such a suspension can also be applied to a carrier material, for example by spraying on or mixing in. The addition of formulation auxiliaries during drying can be of importance for example when a solution or suspension comprising the metabolite is being sprayed. An addition of formulation auxiliaries is effected in particular after drying, for example when applying coatings/coating layers to dried particles. Further adjuvants can be added to the product both after drying and after an optional coating step.

Removing the volatile constituents from the fermentation liquor is effected in a manner known per se by customary methods for separating solid phases from liquid phases, including filtration methods and methods of evaporating volatile constituents of the liquid phases. Such methods, which may also comprise steps for roughly cleaning the products of value and formulation steps, are described, for example in Belter, P. A, Bioseparations: Downstream Processing for Biotechnology, John Wiley & Sons (1988), and Ullmann's Encyclopedia of Industrial Chemistry, 5th ed. on CD-ROM, Wiley-VCH. Methods, equipment, auxiliaries and general or specific embodiments which are known to the skilled worker which can be employed within the scope of product formulation or work up after the fermentation has ended are furthermore described in EP 1038 527, EP 0648 076, EP 835613, EP 0219 276, EP 0394 022, EP 0547 422, EP 1088 486, WO 98/55599, EP 0758 018 and WO 92/12645.

In a first variant of this embodiment, the nonvolatile microbial metabolite, if present in dissolved form in the liquid phase, will be converted from the liquid phase into the solid phase, for example by crystallization or precipitation. Thereafter, the nonvolatile solid constituents, including the metabolite, are separated, for example by means of centrifugation, decanting or filtration. Oily metabolites may also be separated off in a similar manner, the oily fermentation products in question being converted into a solid form by addition of adsorbents, for example silica, silica gels, loam, clay and active charcoal.

In a second variant of this embodiment, the volatile constituents are removed by evaporation. The evaporation can be effected in a manner known per se. Examples of suitable methods for evaporating volatile constituents are spray drying, fluidized-bed drying or fluidized-bed agglomeration, freeze drying, pneumatic driers and contact driers, and extrusion drying. A combination of the abovementioned methods with shape-imparting methods such as extrusion, pelleting or prilling may also be carried out. In these last-mentioned methods, it is preferred to employ partially or largely predried metabolite-comprising substance mixtures.

In a preferred embodiment, the removal of the volatile constituents of the fermentation liquor comprises a spray-drying method or a fluidized-bed drying method, including fluidized-bed granulation. To this end, the fermentation liquor, if appropriate after a preliminary separation for removing coarse solids particles which comprise only small amounts of nonvolatile microbial metabolite, if any, is fed to one or more spray-drying or fluidized-bed-drying apparatuses. The transport, or feeding, of the solids-loaded fermentation liquor is expediently effected by means of customary transport devices for solid-comprising liquids, for example pumps, such as eccentric single-rotor screw pumps (for example from Delasco PCM) or high-pressure pumps (for example from LEWA Herbert Ott GmbH).

A fermentation can also be carried out in such a way that
(i) a portion of not more than 50% by weight, for example in the range of from 5 to 45% by weight, based on the total weight, is removed from the liquid medium (1) obtained in step a2), or its mixture with the further sugar feedstock, and the remainder, if appropriate together with a further sugar feedstock, such as defined above, is supplied to a fermentation for the production of a first metabolite (A), for example a nonvolatile metabolite (A) in solid form or a volatile metabolite (A); and
(ii) the portion which has been removed, if appropriate after previously having removed all or some of the nonstarchy solid constituents of the starch feedstock, if appropriate together with a further sugar feedstock as defined above is supplied to a fermentation for the production of a second metabolite (B), which is identical to, or different from, the metabolite (A).

If the nonstarchy solid constituents of (ii) are separated, the solids content of the remaining portion of the liquid medium amounts to preferably not more than 50% by weight, particularly not more than 30% by weight, especially preferably not more than 10% by weight and very especially preferably not more than 5% by weight. In such a case, it is particularly preferred to separate all of the solid before the fermentation for the production of the second metabolite (B).

This procedure makes possible, in the separate fermentation of (ii), the use of microorganisms for which certain minimum requirements, for example with regard to the oxygen transfer rate, must be met. Suitable microorganisms which are employed in the separate fermentation of (ii) are, for example, *Bacillus* species, preferably *Bacillus subtilis*. The compounds produced by such microorganisms in the separate fermentation are selected in particular from vitamins, cofactors and nutraceuticals, purine and pyrimidine bases, nucleosides and nucleotides, lipids, saturated and unsaturated fatty acids, aromatic compounds, proteins, carotenoids, specifically from vitamins, cofactors and nutraceuticals, proteins and carotenoids, and very specifically from riboflavin and calcium pantothenate.

A preferred embodiment of this procedure relates to parallel production of identical metabolites (A) and (B) in two separate fermentations. This is advantageous in particular in a case where different applications of the same metabolite have different purity requirements. Accordingly, the first metabolite (A), for example an amino acid to be used as feed additive, for example lysine, methionine, threonine or glutamate, is produced using the solids-containing fermentation liquor and the same second metabolite (B), for example the same amino acid to be used as food additive, is produced using the solids-depleted fermentation liquor of (ii). Owing to the complete or partial removal of the non-starchy solid constituents, the complexity of the purification when working up the metabolite whose field of application has a higher purity requirement, for example as food additive, can be reduced.

In a further preferred embodiment, this procedure can be carried out for example as follows. A preferably large-volume fermentation for the production of metabolites A, for example amino acids such as lysine, methionine, glutamate or threonine, of citric acid or of ethanol, is implemented, for example in accordance with the processes described in WO 2005/116228 (PCT/EP2005/005728) or PCT/EP2006/066057 (the earlier application DE 102005042541.0), or in accordance with the known prior art of the fermentative production of bioethanol (see hereinabove). In accordance with (i), some of the liquid medium (1) obtained in step a2) is removed or its mixture with the further sugar feedstock is removed. The portion removed in accordance with (i) can be freed in accordance with (ii) completely or in part from the solids by customary methods, for example centrifugation or filtration, depending on what is required in the fermentation for the production of B. The liquid medium (1) obtained in this way, which is optionally fully or partially freed from the solids, is, in accordance with (ii), fed to a fermentation for the production of a metabolite B, if appropriate together with a further sugar feedstock as defined above. A solids stream separated in accordance with (ii) is advantageously returned to the stream of the sugar-containing liquid medium of the large-volume fermentation.

If the microbial metabolite (A) which is produced in the large-volume fermentation is ethanol this is recovered from the liquid medium (1). The liquid medium (1) should now have sugar contents as are usual in the fermentative production of ethanol (bioethanol), for example in the range of from 20 to 30% by weight. Usually, the remainder of the sugar-containing liquid medium (1) obtained in step (i) is, in this procedure, supplied to the fermentation for the production of A (i.e. in the present case ethanol). The portion of the sugar-containing liquid medium (1) which has been removed in step (i), together with the further sugar feedstock, is supplied to the fermentative production of B, if appropriate after having solids removed in accordance with step (ii).

In a further preferred embodiment of the abovedescribed procedure, the metabolite B produced by the microorganisms in the fermentation is riboflavin. To carry out the fermentation, analogous conditions and procedures as have been described for other carbon feedstocks, for example in WO 01/011052, DE 19840709, WO 98/29539, EP 1186664 and Fujioka, K.: New biotechnology for riboflavin (vitamin B2) and character of this riboflavin. Fragrance Journal (2003), 31(3), 44-48, can be employed.

To carry out this variant of the process, a preferably large-volume fermentation is implemented for the production of metabolites A, for example of amino acids such as lysine, glutamate, threonine or methionine, of citric acid or of ethanol, as described above. In accordance with (i), some of the sugar-containing liquid medium obtained in step a2) is removed and freed in accordance with (ii) completely or in part from the solids by customary methods, for example centrifugation or filtration. The sugar-containing liquid medium obtained therefrom, which is essentially fully or partially freed from the solids, is, after adding a further sugar feedstock, in accordance with (ii), fed to a fermentation for the production of metabolite B, in this case riboflavin. The solids stream separated in accordance with (ii) is advantageously returned to the stream of the sugar-containing liquid medium of the large-volume fermentation.

The riboflavin-containing fermentation liquor which is thus generated in accordance with (ii) can be worked up by analogous conditions and procedures as have been described for other carbon feedstocks, for example in DE 4037441, EP 464582, EP 438767 and DE 3819745. Following lysis of the cell mass, the riboflavin, which is present in crystalline form, is separated, preferably by decanting. Other ways of separating solids, for example filtration, are also possible. Thereafter, the riboflavin is dried, preferably by means of spray dryers and fluidized-bed dryers. As an alternative, the riboflavin-containing fermentation mixture produced in accordance with (ii) can be processed under analogous conditions and using analogous procedures as described in, for example, EP 1048668 and EP 730034. After pasteurization, the fermentation liquor is centrifuged, and the remaining solids-containing fraction is treated with a mineral acid. The riboflavin formed is removed from the aqueous-acidic medium by filtration, washed, if appropriate, and subsequently dried.

In a further preferred embodiment of this procedure, the metabolite B produced by the microorganisms in the fermentation is pantothenic acid. To carry out the fermentation, analogous conditions and procedures as have been described for other carbon feedstocks, for example in WO 01/021772, can be employed.

To carry out this process variant, a procedure such as described above for riboflavin may be followed. The sugar-containing liquid medium (1) which has been subjected to a preliminary purification in accordance with (ii) and which has preferably been essentially freed from the solids, or its mixture with the further sugar feedstock, is fed to a fermentation in accordance with (ii) for the production of pantothenic acid. Here, the fact that the viscosity is reduced in comparison with the solids-containing liquid medium is particularly advantageous. The separated solids stream is preferably returned to the stream of the sugar-containing liquid medium of the large-volume fermentation.

The pantothenic-acid-containing fermentation liquor produced in accordance with (ii) can be worked up under analogous conditions and using analogous procedures as have been described for other carbon feedstocks, for example in EP 1 050 219 and WO 01/83799. After all of the fermentation liquor has been pasteurized, the remaining solids are separated, for example by centrifugation or filtration. The clear runoff obtained in the solids separation step is partly evaporated, if appropriate treated with calcium chloride and dried, in particular spray dried.

The solids which have been separated off can be obtained together with the respective desired microbial metabolite (A) within the scope of the parallel large-volume fermentation process.

After the drying and/or formulation step, whole or milled cereal kernels preferably maize, wheat, barley, millet, triticale and/or rye, may be added to the product formulation or protein composition.

The examples which follow are intended to illustrate individual aspects of the present invention, but are in no way to be understood as limiting.

EXAMPLES

I. Milling the Starch Feedstock

The millbases employed hereinbelow were produced as follows. Whole maize kernels were ground completely using a rotor mill. Using different beaters, milling paths or screen elements, three different degrees of fineness were obtained. A screen analysis of the millbase by means of a laboratory vibration screen (vibration analyzer: Retsch Vibrotronic type VE1; screening time 5 minutes, amplitude: 1.5 mm) gave the results listed in Table I.

TABLE I

| Experiment number | T 70/03 | T 71/03 | T 72/03 |
| --- | --- | --- | --- |
| <2 mm/% | 99.4 | 100 | 100 |
| <0.8 mm/% | 66 | 100 | 99 |
| <0.63 mm/% | 58.6 | 98.5 | 91 |
| <0.315 mm/% | 48.8 | 89 | 65 |
| <0.1 mm/% | | 25 | 9.6 |
| <0.04 mm/% | | 8 | 3.2 |
| Millbase in total | 20 kg | 11.45 kg | 13.75 kg |

II. Enzymatic Starch Liquefaction and Starch Saccharification

II.1. Without Phytase in the Saccharification Step
II.1a) Enzymatic Starch Liquefaction 320 g of dry-milled corn meal (T71/03) were suspended in 480 g of water and admixed with 310 mg of calcium chloride by continuous stirring. Stirring was continued during the entire experiment. After the pH was brought to 6.5 with $H_2SO_4$ and the mixture had been heated to 35° C., 2.4 g of Termamyl 120 L, type L (Novozymes A/S) were added. In the course of 40 minutes, the reaction mixture was heated to a temperature of 86.5° C., the pH being readjusted with NaOH to the above value, if necessary. Within 30 minutes, a further 400 g of the dry-milled corn meal (T71/03) were added, during which process the temperature was raised to 91° C. The reaction mixture was held at this temperature for approximately 100 minutes. A further 2.4 g of Termamyl 120 L were subsequently added and the temperature was held for approximately 100 minutes. The progress of the liquefaction was monitored during the experimentation using the iodine-starch reaction. The temperature was finally raised to 100° C. and the reaction mixture was boiled for a further 20 minutes. At this point in time, starch was no longer detectable. The reactor was cooled to 35° C.

II.1 b) Saccharification

The reaction mixture obtained in II.1a) was heated to 61° C., with constant stirring. Stirring was continued during the entire experiment. After the pH had been brought to 4.3 with $H_2SO_4$, 10.8 g (9.15 ml) of Dextrozyme GA (Novozymes A/S) were added. The temperature was held for approximately 3 hours, during which time the progress of the reaction was monitored with glucose test strips (S-Glucotest by Boehringer). The results are listed in Table II hereinbelow. The reaction mixture was subsequently heated to 80° C. and then cooled. This gave approximately 1180 g of liquid product with a density of approximately 1.2 kg/l and a dry matter content which, as determined by infrared dryer, amounted to approximately 53.7% by weight. After washing with water, a dry matter content (without water-soluble constituents) of approximately 14% by weight was obtained. The glucose content of the reaction mixture, as determined by HPLC, amounted to 380 g/l (see Table 2, sample No. 7).

TABLE II

| Sample No. | min (from addition of glucoamylase) | Glucose concentration in supernatant [g/l] |
| --- | --- | --- |
| 1 | 5 | 135 |
| 2 | 45 | 303 |
| 3 | 115 | 331 |
| 4 | 135 | 334 |
| 5 | 165 | 340 |
| 6 | 195 | 359 |
| 7 | 225 | 380 |

II.2. With Phytase in the Saccharification Step
II.2a) Starch Liquefaction

A dry-milled maize meal sample was liquefied as described in II.1a).

II.2b) Saccharification

The reaction mixture obtained in II.2a) was heated to 61° C. with constant stirring. Stirring was continued during the entire experiment. After the pH had been brought to 4.3 with $H_2SO_4$, 10.8 g (9.15 ml) of Dextrozyme GA (Novozymes A/S) and 70 μl of phytase (700 units of phytase, Natuphyt Liquid 10000 L from BASF AG) were added. The temperature was held for approximately 3 hours, during which time the progress of the reaction was monitored with glucose test strips (S-Glucotest by Boehringer). The reaction mixture was subsequently heated to 80° C. and then cooled. The product obtained was dried by infrared dryer and washed with water. The glucose content of the reaction mixture was determined by HPLC.

II.3 Further Protocols for the Enzymatic Liquefaction and Saccharification of Starch II.3a) Maize Meal 360 g of deionized water were introduced into a reaction vessel. 1.54 ml of $CaCl_2$ stock solution (100 g $CaCl_2 \times 2H_2O$/l) were added to the slurry to a final concentration of approximately 70 ppm $Ca^{2+}$. 240 g of maize meal were slowly run into the water, with constant stirring. After the pH had been brought to 6.5 using 50% by weight strength aqueous NaOH solution, 4.0 ml (=2% by weight enzyme/dry matter) of Termamyl 120 L type L (Novozymes A/S) were added. The slurry was then heated rapidly up to 85° C. During this process, it was necessary to constantly monitor and, if appropriate, adjust the pH.

After the final temperature had been reached, further meal was added, initially 50 g of meal. In addition, 0.13 ml of $CaCl_2$ stock solution was added to the slurry in order to maintain the $Ca^{2+}$ concentration at 70 ppm. During the addition, the temperature was held at a constant 85° C. At least 10 minutes were allowed to pass in order to ensure a complete reaction before a further portion (50 g of meal and 0.13 ml of $CaCl_2$ stock solution) was added. After the addition of two portions, 1.67 ml of Termamyl were added; thereafter, two further portions (in each case 50 g of meal and 0.13 ml of $CaCl_2$ stock solution) were added. A dry-matter content of 55% by weight was reached. After the addition, the temperature was raised to 100° C., and the slurry was boiled for 10 minutes.

A sample was taken and cooled to room temperature. After the sample had been diluted with deionized water (approximately 1:10), one drop of concentrated Lugol's solution (mixture of 5 g of iodine and 10 g of potassium iodide per liter) was added. An intense blue coloration indicated that residual starch was present; a brown coloration was observed when all of the starch had been hydrolyzed. When the test indicated that a portion of residual starch was present, the temperature was again lowered to 85° C. and kept constant. A further 1.67 ml of Termamyl were added until the iodine-starch reaction was negative.

For the subsequent saccharification reaction, the mixture, which tested negative for starch, was brought to 61° C. The pH was brought to 4.3 by addition of 50% strength sulfuric acid. In the course of the reaction, the pH was maintained at this value. The temperature was maintained at 61° C. 5.74 ml (=1.5% by weight enzyme/dry matter) of Dextrozym GA (Novozymes A/S) were added in order to convert the liquefied starch into glucose. The reaction was allowed to proceed for one hour. To inactivate the enzyme, the mixture was heated at 85° C. The hot mixture was filled into sterile containers, which were cooled and then stored at 4° C. A final glucose concentration of 420 g/l was obtained.

II.3b) Rye Meal (Including Pretreatment with Cellulase/Hemicellulase)

360 g of deionized water were introduced into a reaction vessel. 155 g of rye meal were slowly run into the water, with constant stirring. The temperature was maintained at a constant 50° C. After the pH had been brought to 5.5 using 50% by weight strength of aqueous NaOH solution, 3.21 ml (=2.5% by weight enzyme/dry matter) of Viscozyme L (Novozymes A/S) were added. After 30 minutes, a further meal was added, with 55 g of meal being added initially. After a further 30 minutes, a further 50 g of meal were added; 30 minutes later, a further 40 g of meal were added. 30 minutes after the last addition, the liquefaction could be started.

1.7 ml of CaCl$_2$ stock solution (100 g CaCl$_2$×2H$_2$O/l) were added. After the pH had been adjusted to 6.5 using 50% by weight of aqueous NaOH solution, 5.0 ml (=2% by weight enzyme/dry matter) of Termamyl 120 L type L (Novozymes A/S) were added. The slurry was then heated rapidly at 85° C. During this process, the pH was continuously monitored and, if appropriate, adjusted.

After the final temperature had been reached, further meal was added, initially 60 g of meal. In addition, 0.13 ml of CaCl$_2$ stock solution was added to the slurry in order to maintain the Ca$^{2+}$ concentration at 70 ppm. During the addition, the temperature was held at a constant 85° C. At least 10 minutes were allowed to pass in order to ensure a complete reaction before a further portion (40 g of meal and 0.1 ml of CaCl$_2$ stock solution) was added. 1.1 ml of Termamyl were added; thereafter, a further portion (40 g of meal and 0.1 ml of CaCl$_2$ stock solution) was added. A dry-matter content of 55% by weight was reached. After the addition, the temperature was raised to 100° C., and the slurry was boiled for 10 minutes.

A sample was taken and cooled to room temperature. After the sample had been diluted with deionized water (approximately 1:10), one drop of concentrated Lugol's solution (mixture of 5 g of iodine and 10 g of potassium iodide per liter) was added. An intense blue coloration indicated that residual starch was present; a brown coloration was observed when all of the starch had been hydrolyzed. When the test indicated that a portion of residual starch was present, the temperature was again lowered to 85° C. and kept constant. A further 1.1 ml of Termamyl were added until the iodine-starch reaction was negative.

For the subsequent saccharification reaction, the mixture, which tested negative for starch, was brought to 61° C. The pH was brought to 4.3 by addition of 50% strength sulfuric acid. In the course of the reaction, the pH was maintained at this value. The temperature was maintained at 61° C. 5.74 ml (=1.5% by weight enzyme/dry matter) of Dextrozym GA (Novozymes A/S) were added in order to convert the liquefied starch into glucose. The reaction was allowed to proceed for one hour. To inactivate the enzyme, the mixture was heated at 85° C. The hot mixture was filled into sterile containers, which were cooled and then stored at 4° C. A final glucose concentration of 370 g/l was obtained.

II.3c) Wheat Meal (Including Pretreatment with Xylanase)

360 g of deionized water were introduced into a reaction vessel. The water was heated at 55° C., and the pH was adjusted to 6.0 using 50% by weight strength aqueous NaOH solution. After the temperature and the pH had been adjusted, 3.21 ml (=2.5% by weight enzyme/dry matter) of Shearzyme 500 L (Novozymes A/S) were added. 155 g of wheat meal were slowly run into the solution, with constant stirring. The temperature and the pH were kept constant. After 30 minutes, a further meal was added, with 55 g of meal being added initially. After a further 30 minutes, a further 50 g of meal were added; 30 minutes later, a further 40 g of meal were added. 30 minutes after the last addition, the liquefaction could be started.

The liquefaction and saccharification were carried out as described in II.3b. A final glucose concentration of 400 g/l was obtained.

III. Strain ATCC13032 lysCfbr

In some of the examples which follow, a modified *Corynebacterium glutamicum* strain, which has been described in WO 05/059144 under the name ATCC13032 lysCfbr, was employed.

Example 1

In each case one maize, wheat and rye meal hydrolyzate was prepared as described under 1) hereinbelow. The total sugar content in each of these media was increased by adding various sugar solutions (comprising glucose, crude sugar, melasses). The media were employed in shake-flask experiments using *Corynebacterium glutamicum* (ATCC13032 lysC$^{fbr}$) and *Bacillus* PA824 (described in detail in WO 02/061108) as carbon feedstock.

1) Preparation of the Meal Hydrolyzate
a) Maize Meal Hydrolyzate 360 g of deionized water were introduced into a reaction vessel. 155 g of corn meal were slowly run into the water, with constant stirring.

Liquefaction

After the pH had been brought to 5.8 using 50% by weight strength aqueous NaOH solution, 2.6 ml (=2% by weight enzyme/dry matter) of Liquozyme SC (from Novozymes A/S) were added. The slurry was then heated rapidly to 100° C. and boiled for 10 minutes. During this process, the pH was constantly monitored and, if appropriate, adjusted.

A sample was taken and cooled to room temperature. After the sample had been diluted with deionized water (approximately 1:10), one drop of concentrated Lugol's solution (mixture of 5 g of iodine and 10 g of potassium iodide per liter) was added. An intense blue coloration indicated that residual starch was present; a brown coloration was observed when all of the starch had been hydrolyzed.

Saccharification

For the subsequent saccharification reaction, the mixture, which tests negative for starch, was brought to 61° C. The pH was brought to 4.3 by addition of 50% strength sulfuric acid. In the course of the reaction, the pH was maintained at this value. The temperature was maintained at 61° C. 2.0 ml (=1.5% by weight enzyme/dry matter) of Dextrozym GA (Novozymes A/S) were added in order to convert the liquefied starch into glucose. The reaction was allowed to proceed for one hour. To inactivate the enzyme, the mixture was heated at 85° C. The hot mixture was filled into sterile containers, which were cooled and then stored at 4° C.

b) Wheat Meal Hydrolyzate

Xylanase Pretreatment 360 g of deionized water were introduced into a reaction vessel. The water was heated at 55° C., and the pH was adjusted to 6.0 using 50% by weight strength aqueous NaOH solution. After the temperature and the pH were adjusted, 3.21 ml (=2.5% by weight enzyme/dry matter) of Shearzyme 500 L (Novozymes A/S) were added. 155 g of wheat meal were slowly run into the solution, with constant stirring. The temperature and the pH were kept constant. 30 minutes after the last addition, the liquefaction could be started.

The liquefaction and saccharification were carried out as described in 1a).

c) Rye Meal Hydrolyzate

Pretreatment with Cellulase/Hemicellulase 360 g of deionized water were introduced into a reaction vessel. 155 g of rye meal were slowly run into the water, with constant stirring. The temperature was maintained at a constant 50° C. After the pH was brought to 5.5 using 50% by weight strength of sulfuric acid, 3.21 ml (=2.5% by weight enzyme/dry matter) of Viscozyme L (Novozymes A/S) were added. 30 minutes after the last addition, the liquefaction could be started.

The liquefaction and saccharification were carried out as described in 1a).

2) Preparation of the Inoculum a) For *Corynebacterium glutamicum*

The cells were streaked onto sterile CM+CaAc agar (composition: see Table 1; minutes at 121° C.) and then incubated overnight at 30° C. The cells were subsequently scraped from the plates and resuspended in saline. 25 ml of the medium (see Table 4) in 250 ml Erlenmeyer flasks equipped with two baffles were inoculated in each case with such an amount of the cell suspension thus prepared that the optical density reached an OD610 value of 0.5 at 610 nm.

TABLE 1

Composition of the CM + CaAc agar plates

| Concentration | Constituent |
| --- | --- |
| 10.0 g/l | D-glucose |
| 2.5 g/l | NaCl |
| 2.0 g/l | Urea |
| 5.0 g/l | Bacto peptone (Difco) |
| 5.0 g/l | Yeast extract (Difco) |
| 5.0 g/l | Beef extract (Difco) |
| 20.0 g/l | Casamino acids |
| 20.0 g/l | Agar | b) For *Bacillus*

42 ml of the preculture medium (see Table 2) in 250 ml Erlenmeyer flasks equipped with two baffles were inoculated in each case with 0.4 ml of a frozen culture and incubated for 24 hours at 43° C. with shaking (250 rpm) in a humidified shaker.

TABLE 2

Composition of the preculture medium

| Constituent | Concentration |
| --- | --- |
| Maltose | 28.6 g/l |
| Soya meal | 19.0 g/l |
| $(NH_4)_2SO_4$ | 7.6 g/l |
| Monosodium glutamate | 4.8 g/l |
| Sodium citrate | 0.95 g/l |
| $FeSO_4 \times 7\,H_2O$ | 9.5 mg/l |
| $MnCl_2 \times 4\,H_2O$ | 1.9 mg/l |
| $ZnSO_4 \times 7\,H_2O$ | 1.4 mg/l |
| $CoCl_2 \times 6\,H_2O$ | 1.9 mg/l |
| $CuSO_4 \times 5\,H_2O$ | 0.2 mg/l |
| $Na_2MoO_4 \times 2\,H_2O$ | 0.7 mg/l |
| $K_2HPO_4 \times 3\,H_2O$ | 15.2 g/l |
| $KH_2PO_4$ | 3.9 g/l |
| $MgCl_2 \times 6\,H_2O$ | 0.9 g/l |
| $CaCl_2 \times 2\,H_2O$ | 0.09 g/l |
| MOPS | 59.8 g/l |
| pH* | 7.2 |

*to be adjusted with dilute aqueous KOH solution 42 ml of the main culture medium (see Table 6) in 250 ml Erlenmeyer flasks equipped with two baffles were inoculated in each case with 1 ml of preculture.

3) Preparation of the Fermentation Liquor a) For *Corynebacterium glutamicum*

The composition of the flask medium is listed in Table 4. It should have an initial sugar concentration of 60 g/l. Half of the sugar originated from the hydrolyzate (fermentation medium (1)), while the other half was added in the form of a sugar solution. To this end, a mixture of hydrolyzate and sugar solution was prepared and added to the flask medium. A corresponding amount of glucose solution was used in the control medium.

Preparation of the Meal Hydrolyzates with Added Sugar

The following solutions were prepared (see Table 3):

TABLE 3

Preparation of the meal hydrolyzates with added sugar

| Meal hydrolyzate | Glucose concentration in the hydrolyzate [g/l] | Hydrolyzate per liter reaction mixture [ml] | Sugar solution | Concentration in the sugar solution [g/l] | Sugar solution per liter of reaction mixture [ml] |
| --- | --- | --- | --- | --- | --- |
| Maize 30% | 250.0 | 240 | Glucose | 626 | 96 |
| Maize 30% | 250.0 | 240 | Crude sugar | 639 | 94 |
| Wheat 30% | 258.9 | 232 | Glucose | 626 | 96 |

TABLE 3-continued

Preparation of the meal hydrolyzates with added sugar

| Meal hydrolyzate | Glucose concentration in the hydrolyzate [g/l] | Hydrolyzate per liter reaction mixture [ml] | Sugar solution | Concentration in the sugar solution [g/l] | Sugar solution per liter of reaction mixture [ml] |
|---|---|---|---|---|---|
| Wheat 30% | 258.9 | 232 | Crude sugar | 639 | 94 |
| Rye 30% | 217.9 | 275 | Glucose | 626 | 96 |
| Rye 30% | 217.9 | 275 | Crude sugar |  | 94 |

TABLE 4

Flask medium

| Meal hydrolyzate with sugar solution | 500 ml/l |
|---|---|
| $(NH_4)_2SO_4$ | 20 g/l |
| Urea | 5 g/l |
| $KH_2PO_4$ | 0.113 g/l |
| $K_2HPO_4$ | 0.138 g/l |
| ACES | 52 g/l |
| MOPS | 21 g/l |
| Citric acid × $H_2O$ | 0.49 g/l |
| 3,4-Dihydroxybenzoic acid | 3.08 mg/l |
| NaCl | 2.5 g/l |
| KCl | 1 g/l |
| $MgSO_4 \times 7\ H_2O$ | 0.3 g/l |
| $FeSO_4 \times 7\ H_2O$ | 25 mg/l |
| $MnSO_4 \times 4\text{-}6\ H_2O$ | 5 mg/l |
| $ZnCl_2$ | 10 mg/l |
| $CaCl_2$ | 20 mg/l |
| $H_3BO_3$ | 150 µg/l |
| $CoCl_2 \times 6\ H_2O$ | 100 µg/l |
| $CuCl_2 \times 2\ H_2O$ | 100 µg/l |
| $NiSO_4 \times 6\ H_2O$ | 100 µg/l |
| $Na_2MoO_4 \times 2\ H_2O$ | 25 µg/l |
| Biotine (Vit. H) | 1050 µg/l |
| Thiamine × HCl (Vit $B_1$) | 2100 µg/l |
| Nicotinamide | 2.5 mg/l |
| Pantothenic acid | 125 mg/l |
| Cyanocobalamine (Vit $B_{12}$) | 1 µg/l |
| 4-Aminobenzoic acid (PABA; Vit. $H_1$) | 600 µg/l |
| Folic acid | 1.1 µg/l |
| Pyridoxin (Vit. $B_6$) | 30 µg/l |
| Riboflavin (Vit. $B_2$) | 90 µg/l |
| CSL | 40 ml/l |
| pH* | 6.85 |

*to be adjusted with dilute aqueous NaOH solution

After the inoculation, the flasks were incubated for 3 days at 30° C. and with shaking (200 rpm) in a humidified shaker. After the fermentation was terminated, the lysine content was determined by HPLC. The HPLC analyses were carried out with an Agilent 1100 series LC system. The amino acid concentration was determined by means of high-pressure liquid chromatography on an Agilent 1100 series LC System HPLC. Pre-column derivatization with ortho-phthaldehyde permits the quantification of the amino acid formed; the amino acid mixture is separated using an Agilent Hypersil AA column. The results are compiled in Table 5.

TABLE 5

Means

| Meal hydrolyzate | Sugar solution | Lysine [g/l] | Yield* |
|---|---|---|---|
| Maize | Glucose | 12.50 | 0.21 |
|  | Crude sugar | 10.64 | 0.19 |
|  | Melasses | 10.06 | 0.18 |
| Wheat | Glucose | 10.82 | 0.18 |
|  | Crude sugar | 10.14 | 0.18 |
|  | Melasses | 9.67 | 0.17 |
| Rye | Glucose | 10.89 | 0.18 |
|  | Crude sugar | 9.59 | 0.16 |
|  | Melasses | 9.67 | 0.16 |
| Control |  | 11.54 | 0.20 |

*based on total glucose equivalents b) For *Bacillus*

The composition of the flask medium is listed in Table 6. It should have an initial glucose concentration of 28.6 g/l. Half of the sugar originated from the hydrolyzate, while the other half was added in the form of a glucose solution. A corresponding amount of glucose solution was used in the control medium.

TABLE 6

Flask media

| Maize | 250 g/l † | 57 ml/l ‡ |  |
|---|---|---|---|
| Wheat | 259 g/l † |  | 55 ml/l ‡ |
| Rye | 218 g/l † |  | 67 ml/l ‡ |
| Glucose solution (c = 626 g/l) |  | 23 ml/l |  |
| Soya meal |  | 19.0 g/l |  |
| $(NH_4)_2SO_4$ |  | 7.6 g/l |  |
| Monosodium glutamate |  | 4.8 g/l |  |
| Sodium citrate |  | 0.95 g/l |  |
| $FeSO_4 \times 7\ H_2O$ |  | 9.5 mg/l |  |
| $MnCl_2 \times 4\ H_2O$ |  | 1.9 mg/l |  |
| $ZnSO_4 \times 7\ H_2O$ |  | 1.4 mg/l |  |
| $CoCl_2 \times 6\ H_2O$ |  | 1.9 mg/l |  |
| $CuSO_4 \times 5\ H_2O$ |  | 0.2 mg/l |  |
| $Na_2MoO_4 \times 2\ H_2O$ |  | 0.7 mg/l |  |
| $K_2HPO_4 \times 3\ H_2O$ |  | 15.2 g/l |  |
| $KH_2PO_4$ |  | 3.9 g/l |  |
| $MgCl_2 \times 6\ H_2O$ |  | 0.9 g/l |  |
| $CaCl_2 \times 2\ H_2O$ |  | 0.09 g/l |  |
| MOPS |  | 59.8 g/l |  |
| pH* |  | 7.2 |  |

*to be adjusted with dilute aqueous NaOH solution
† glucose concentration in the hydrolyzate
‡ required amount of weighed-in hydrolyzate per liter of medium After the inoculation, the flasks were incubated for 24 hours at 43° C. and with shaking (250 rpm) in a humidified shaker. After the fermentation was terminated, the glucose and pantothenic acid contents were determined by HPLC. The glucose was determined with the aid of an Aminex HPX-87H column from Bio-Rad. The pantothenic acid concentration was determined via separation on a Aqua C18 column (Phenomenex).

The results are compiled Table 7.

TABLE 7

| | Means after 24 h | |
|---|---|---|
| | Pantothenic acid, t = 24 h [g/l] | Yield [g pantothenic acid/g glucose] |
| Maize | 2.7 | 0.09 |
| Wheat | 2.4 | 0.08 |
| Rye | 2.7 | 0.09 |
| Control | 2.7 | 0.09 |

The invention claimed is:

1. A process for the fermentative production of at least one organic compound having at least 3 C atoms or having at least 2 C atoms and at least one 1 N atom, wherein the organic compound is selected among the group consisting of mono-, di- and tricarboxylic acids, which optionally have hydroxyl groups attached to them and which have 3 to 10 carbon atoms, proteinogenic and nonproteinogenic amino acids, purine bases, pyrimidine bases; nucleosides, nucleotides, lipids; saturated and unsaturated fatty acids; diols having 4 to 10 carbon atoms, polyhydric alcohols having 3 or more hydroxyl groups, long-chain alcohols having at least 4 carbon atoms, carbohydrates, aromatic compounds, vitamins, provitamins, cofactors, nutraceuticals, proteins, carotenoids, ketones having 3 to 10 carbon atoms, lactones, biopolymers and cyclodextrins, the process comprising the following steps:
 a1) milling a starch feedstock selected from cereal kernels, thus obtaining a millbase which comprises at least 50% by weight of the nonstarchy solid constituents which are present in the milled cereal kernels and where the nonstarchy constituents in the millbase amount to at least 15% by weight;
 a2) suspending the millbase in an aqueous liquid and hydrolysis of the starch portion in the millbase by enzymatic liquefaction and, if appropriate, subsequent saccharification, whereby a liquid (1) which comprises mono- or oligosaccharides and non-starchy constituents of the millbase is obtained; and
 b) addition of liquid (1) which comprises mono- or oligosaccharides together with metabolizable mono-, di- or oligosaccharides or together with a composition which comprises metabolizable mono-, di- or oligosaccharides in a concentration of at least 50% by weight and which is free from solids which are insoluble in water to a fermentation medium comprising a microorganism which is capable of overproducing the organic compound under fermentation conditions, wherein the total mono-, di- and oligosaccharide concentration in the liquid (1) is increased by at least 50 g/kg by adding metabolizable mono-, di- or oligosaccharides or by adding a medium which comprises metabolizable mono-, di- or oligosaccharides in a concentration of at least 50% by weight and which is essentially free from solids which are insoluble in water.

2. The process according to claim 1, wherein the total mono-, di- and oligosaccharide concentration of the liquid (1) obtained in step a2) is in the range of from 100 to 400 g/kg.

3. The process according to claim 1, wherein the amount of mono-, di- or oligosaccharides introduced into the fermentation by addition of the liquid (1) accounts for 40 to 95% by weight of the total amount of mono-, di- and oligosaccharides introduced into the fermentation.

4. The process according to claim 1, wherein the total mono-, di- and oligosaccharide concentration in the liquid (1) is increased to a value in the range of from 450 to 600 g/kg.

5. The process according to claim 1, wherein the employed composition which comprises metabolizable mono- or oligosaccharides is a by-product of sugar production comprising glucose or sucrose and, if appropriate, dextrins.

6. The process according to claim 5, wherein the employed composition comprising metabolizable mono- or oligosaccharides is molasses from the beet sugar production.

7. The process according to claim 1, wherein, in step a2), at least a portion of the mill base obtained in step a1) is hydrolyzed by adding it, continuously or batchwise, to the aqueous liquid under hydrolysis conditions.

8. The process according to claim 1, wherein, in step a2), the suspension of the millbase is heated above the gelatinization temperature of the starch present in the millbase by introducing steam into the suspension.

9. The process according to claim 1, wherein the microorganism employed for the fermentation is selected among the group consisting of natural or recombinant microorganisms which overproduce at least one of the following metabolites: enzymes, amino acids, vitamins, disaccharides, aliphatic mono- and dicarboxylic acids having 3 to 10 C atoms, aliphatic hydroxycarboxylic acids having 3 to 10 C atoms, ketones having 3 to 10 C atoms, alkanols having 4 to 10 C atoms, alkanediols having 3 to 8 C atoms, and polyhydroxyalkanoates.

10. The process according to claim 1, wherein the microorganisms are selected among the group of genera consisting of *Corynebacterium, Bacillus, Ashbya, Escherichia, Aspergillus, Alcaligenes, Actinobacillus, Anaerobiospirillum, Lactobacillus, Propionibacterium, Clostridium*, and *Rhizopus*.

11. The process according to claim 9, wherein the microorganism employed for the fermentation is selected among natural or recombinant microorganisms which overproduce amino acids.

12. The process according to claim 10, wherein the microorganism is a strain of the genus *Corynebacterium*.

13. The process according to claim 9, wherein the microorganism employed for the fermentation is selected among natural or recombinant microorganisms which overproduce an enzyme.

14. The process according to claim 13, wherein the microorganism is selected among phytase-overproducing microorganisms.

15. The process according to claim 1, wherein the organic compound is depleted or isolated from the fermentation liquor and the volatile constituents of the fermentation liquor are subsequently removed, a solid or semisolid protein composition being obtained.

16. The process according to claim 1, wherein at least some of the volatile constituents of the fermentation liquor are removed without previous isolation or depletion of a nonvolatile microbial metabolite and, if appropriate, without previous removal of solid constituents, a solid formulation of a nonvolatile microbial metabolite being obtained.

17. The process according to claim 2, wherein the amount of mono-, di- or oligosaccharides introduced into the fermentation by addition of the liquid (1) accounts for 40 to 95% by weight of the total amount of mono-, di- and oligosaccharides introduced into the fermentation.

18. The process according to claim 1, wherein the millbase obtained in step a1) comprises at least 90% by weight of the non-starchy solid constituents which are present in the milled cereal kernels.

* * * * *